US008242058B2

(12) United States Patent  (10) Patent No.: US 8,242,058 B2
Raines et al.  (45) Date of Patent: Aug. 14, 2012

(54) REAGENTS AND METHODS FOR APPENDING FUNCTIONAL GROUPS TO PROTEINS

(75) Inventors: Ronald T. Raines, Madison, WI (US); Jeet Kalia, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 516 days.

(21) Appl. No.: 11/781,838

(22) Filed: Jul. 23, 2007

(65) Prior Publication Data

US 2008/0020942 A1    Jan. 24, 2008

Related U.S. Application Data

(60) Provisional application No. 60/820,011, filed on Jul. 21, 2006.

(51) Int. Cl.
*C40B 60/14* (2006.01)
*C07H 21/04* (2006.01)

(52) U.S. Cl. .............. 506/40; 506/37; 506/32; 506/18; 530/345; 530/402

(58) Field of Classification Search .................. 506/40, 506/32, 37, 18; 530/345, 402
See application file for complete search history.

(56) References Cited

U.S. PATENT DOCUMENTS

| | | | |
|---|---|---|---|
| 4,206,231 A | 6/1980 | Haeckel et al. | |
| 6,972,320 B2 | 12/2005 | Raines et al. | |
| 6,974,884 B2 | 12/2005 | Raines et al. | |
| 7,230,068 B2 * | 6/2007 | Wilson | 528/407 |
| 7,256,259 B2 | 8/2007 | Raines et al. | |
| 7,414,106 B2 * | 8/2008 | Camarero et al. | 530/333 |

FOREIGN PATENT DOCUMENTS

WO    WO 01/87920    11/2001

OTHER PUBLICATIONS

Accession No. 80:27004 from USPATFULL; listing U.S. Patent No. 4,206,231 and showing the compound with Registry No. 70082-33-6.*
Bednar et al. (1990) "Reactivity and pH Dependence of Thiol Conjugation to N-ethylmaleimide: Detection of a Conformational Change in Chalcone Isomerase," *Biochemistry* 29(15):3684-3690.
Bonnet et al. (2001) "Chemoselective Acylation of Fully Deprotected Hydrazino Acetyl Peptides. Application to the Synthesis of Lipopeptides," *J. Org. Chem.* 66(2):443-449.
Borodovsky et al. (Oct. 2002) "Chemistry-Based Functional Proteomics Reveals Novel Members of the Deubiquitinating Enzyme Family," *Chem. Biol.* 9(10):1149-1159.
Bruice et al. (1967) "Aminolysis of Phenyl Acetates in Aqueous Solutions. VII Observations on the Influence of Salts, Amine Structure, and Base Strength," *J. Am. Chem. Soc.* 89(9):2106-2121.
Bruice et al. (1963) "Nucleophile Displacement Reactions at the Thiol-Ester Bond of δ-Thiolvalerolactone," *J. Am. Chem. Soc.* 85(11):1659-1669.

Bruice et al. (1964) "The Kinetic Demonstration of a Metastable Intermediate in a Nucleophilic Displacement at a Thiol-Ester Bond," *J. Am. Chem. Soc.* 86(4):738-739.
Bruice et al. (1964) "O- vs. N-Attack of Hydroxylamine on the n-Butyl Thiolacetate and the Establishment that N-Attack Passes through a Metastable Intermediate," *J. Am. Chem. Soc.* 86(4):739-740.
Bruice et al. (1964) "Nucleophilic Displacement Reactions at the Thiolester Bond. III. Kinetic Demonstration of Metastable Intermediates in the Hydroxylaminolysis and Methoxylaminolysis of Thiolesters and Thiolactones in Aqueous Solutions," *J. Am. Chem. Soc.* 86(22):4886-4897.
Buncel et al. (Aug. 2004) "The α-Effect and its Modulation by Solvent," *Tetrahedron* 60(36):7801-7825.
Castro et al. (1999) "Kinetics and Mechanisms of Reactions of Thiol, Thiono, and Dithio Analogues of Carboxylic Esters with Nucleophiles," *Chem. Rev.* 99(12):3505-3524.
Cha et al. (2005) "Enzymatic Activity on a Chip: The Critical Role Protein Orientation," *Proteomics* 5:416-419.
Cottingham et al. (2001) "A Method for the Amidation of Recombinant Peptides Expressed as Intein Fusion Proteins in *Escherichia coli*," *Nat. Biotehcnol.* 19:974-977.
Dawson et al. (2000) "Synthesis of Native Proteins by Chemical Ligation," *Ann. Rev. Biochem.* 69:923-960.
Duckworth et al. (2006) "Site-Specific, Covalent Attachment of Proteins to a Solid Surface," *Bioconjug. Chem.* 17:967-974.
Evans et al. (2002) "Mechanistic and Kinetic Considerations of Protein Splicing," *Chem. Rev.* 102(12):4869-4883.
Friedman et al. (1999) "Lysinoalanine in Food and in Antimicrobial Proteins," *Adv. Exp. Med. Bio.* 459:145-159. Gauchet et al. (2006) "Regio- and Chemoselective Covalent Immobilization of Proteins Through Unnatural Amino Acids," *J. Am. Chem. Soc.* 128:9274-9275.
Gregory et al. (1967) "Nucleophilic Displacement Reactions at the Thiol Ester Bond. V. Reactions of 2,2,2-Trifluoroethyl Thiolacetate," *J. Am. Chem. Soc.* 89(9):2121-2127.

(Continued)

*Primary Examiner* — Teresa Wessendorf
(74) *Attorney, Agent, or Firm* — Greenlee Sullivan P.C.

(57) ABSTRACT

Methods and reagents for site-selective functionalization of peptides and proteins. The methods most generally involve the reaction of a thioester with hydrazine. Reagents include bifunctional reagents of formula:

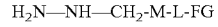

$H_2N-NH-CH_2-M-L-FG$ and salts thereof where M is a single bond or a chemical group carrying a non-bonding electron pair, such as —C(O)NR'—, where R' is H, or an alkyl or aryl group; L is an optional linker group as described above; and FG is a functional group having reactivity that is orthongonal to that of the hydrazine group. FG can, among others, be an azide, alkenyl, alkynyl, nitrile (—CN) or triazole group and is preferably an azide group (—$N_3$). Methods and reagents can, for example, be combined with intein-mediated protein splicing to link proteins or fragments thereof to various chemical species or to a surface. Surface immobilization of proteins via the methods herein results in immobilized proteins which substantially retain biological activity and is thus useful for the generation of peptide or protein microarrays. Kits for functionalization and/or immobilization of peptides and proteins are provided as well as microarrays of peptides, proteins or both.

37 Claims, 8 Drawing Sheets

OTHER PUBLICATIONS

Huisgen et al. (1963) "1,3-Dipolar Cycloadditions Past and Future," *Angew. Chem. Int. Ed. Engle.* 2(10):565-598.

Jencks et al. (1960) "Reactivity of Nucleophilic Reagents Toward Esters," *J. Am. Chem. Soc.* 82(7):1778-1786.

Jencks, W.P. (1958) "The Reaction of Hydroxylamine with Activated Acyl Groups. II. Mechanism of the Reaction," *J. Am. Chem. Soc.* 80(17):4585-4588.

Jencks, W.P. (1958) "The Reaction of Hydroxylamine with Activated Acyl Groups. I. Formation of O-Acylhydroxylamine," *J. Am. Chem. Soc.* 80(17):4581-4584.

Kalia et al. (2006) "Reactivity of Intein Thioesters: Appending a Functional Group to a Protein," *Chembiochem.* 7:1375-1383.

Kiick et al. (Jan. 2002) "Incorporation of Azides into Recombinant Proteins for Chemoselestive Modification by the Staudinger Ligation," *Proc. Nat. Acad. Sci. USA* 99(1):19-24.

Kluger et al. (1984) "Aminolysis of Maleic Anhydride. Kinetics and Thermodynamics of Amide Formation," *J. Am. Chem. Soc.* 106:5667-5670.

Kolb et al. (Dec. 15, 2003) "The Growing Impact of Click Chemistry on Drug Discovery," *Drug. Disc. Today* 8(24):1128-1137.

Kwon et al. (2006) "Selective Immobilization of Proteins onto Solid Supports Through Spoit-Intein-Mediated Protein Trans-Splicing," *Angew. Chem. Int. Ed. Engle.* 45:1726-1729.

Lesaicherre et al. (2002) "Intein-Mediated Biotinylation of Proteins and Its Application in a Protein Micrarray," *J. Am. Chem. Soc.* 124(30):8768-8769.

Lesaicherre et al. (Aug. 2002) "Developing Site-Specific Immobilization Strategies of Peptides in a Microarray," *Bioorg. Med. Chem. Lett.* 12(16):2079-2083.

Lue et al. (2004) "Versatile Protein Biotinylation Strategies for Potential High-Throughput Proteomics," *J. Am. Chem. Soc.* 126(4):1055-1062.

Muir. T.W. (2003) "Semisynthesis of Proteins by Expressed Protein Ligation," *Ann. Rev. Biochem.* 72:249-289.

Muralidharan et al. (Jun. 2006) "Protein Ligation: An Enabling Technology for the Biophysical Analysis of Proteins," *Nat. Methods* 3(6):429-438.

Nilsson et al. (2003) "Protein Assembly by Orthogonal Chemical Ligation Methods," *J. Am. Chem. Soc.* 125(18):5268-5269.

Nilsson et al. (2001) "High-Yielding Staudinger Ligation of a Phosphinothioester and Azide to From a Peptide," *Org. Lett.* 3(1):9-12.

Nilsson et al. (2005) "Chemical Synthesis of Proteins," *Ann. Rev. Biophys. Biomol. Struct.* 34:91-118.

Noda et al. (1953) "Properties of Thiolesters: Kinetics of Hydrolysis in Dilute Aqueous Media," *J. Am. Chem. Soc.* 75(4):913-917.

Noren et al. (1989) "A General Method for Site-Specific Incorporation of Unnatural Amino Acids into Proteins," *Science* 244:182-188.

Paulus, H. (2000) "Protein Splicing and Related Forms of Protein Autoprocessing," *Ann. Rev. Biochem.* 69:447-496.

Raines et al. (1997) "Nature's Transitory Covalent Bond," *Nat. Struct. Biol.* 4:424-427.

Soellner et al. (2002) "Staudinger Ligation of α-Azido Acids Retains Stereochemistry," *J. Org. Chem.* 67(14):4993-4996.

Soellner et al. (2003) "Site-Specific Immobilization by Staudinger Ligation," *J. Am. Chem. Soc.* 125(39):11790-11791.

Speers et al. (2003) "Activity-Based Protein Profiling in Vivo Using a Copper(I)-Catalyzed Azide-Alkyne [3+2] Cycloaddition," *J. Am. Chem. Soc.* 125(16):4686-4687.

Staudinger et al. (1919) "Über neue organische Phosphorverbindungen III. Phosphinmethylendervate and Phosphinimine," *Helv. Chim. Acta.* 2(1):635-646.

Sun et al. (2006) "Carbohydrate and Protein Immobilization onto Solid Surfaces by Sequential Diels-Alder and Azide-Alkyne Cycloadditions," *Bioconjug. Chem.* 17(1):52-57.

Tan et al. (2005) "Intein-Mediated, In Vitro and In Vivo Protein Modifications with Small Molecules," *Protein Pept. Lett.* 12:769-775.

Terrettax et al. (2002) "Stable Self-Assembly of a Protein Engineering Scaffold on Gold Surfaces," *Protein Sci.* 11:1917-1925.

Tolbert et al. (2000) "Intein-Mediated Synthesis of Proteins Containing Carbohydrates and Other Molecular Probes," *J. Am. Chem. Soc.* 122(23):5421-5428.

Watzke et al. (2006) "Site-Selective Protein Immobilization by Staudinger Ligation," *Angew. Chem. Int. Ed. Engle.* 45:1408-1412.

Wood et al. (2004) "Optimized Conjugation of a Fluorescent Label to Proteins Via Intein-Mediated Activation and Ligation," *Bioconjug. Chem.* 15(2):366-372.

Woo, et al. (2007) "The Use of Aryl Hydrazide Linkers for the Solid Phase Synthesis of Chemically Modified Peptides," *Intn'l J. of Peptide Research and Therapeutics*, vol. 13, Nos. 1-2, pp. 181-190.

\* cited by examiner when H-Nu is H₂N-NH-R

REAGENTS AND METHODS FOR APPENDING FUNCTIONAL GROUPS TO PROTEINS

STATEMENT REGARDING GOVERNMENT SUPPORT

This invention was made with United States government support awarded by the following agencies: National Institutes of Health (NIH) GM044783. The United States government has certain rights in this invention.

CROSS-REFERENCE TO RELATED APPLICATIONS

This application takes priority from U.S. provisional application Ser. No. 60/820,011, filed Jul. 21, 2006, which is incorporated by reference in its entirety herein.

BACKGROUND OF THE INVENTION

The success of genome sequencing has heightened the demand for new means to manipulate proteins. An especially desirable goal is the ability to modify a target protein or peptide at a specific site with a functional group of orthogonal reactivity which can in turn be used for protein modification or immobilization.

Site-specific derivatization of proteins and peptides is useful in a variety of research and therapeutic applications. For example, attachment of reporter molecules (labels or tags) can be used to detect the proteins or peptides. Attachment of ligands which bind to a receptor or other binding partner can, for example, be used to facilitate protein or peptide detection, isolation or purification. Linking of therapeutic proteins to other proteins or peptides, or to ligands or other small molecules, for example, can enhance their therapeutic value.

Site-specific derivatization of proteins and peptides is also useful for their immobilization onto surfaces. Microarrays in which proteins, peptides or other chemical species are immobilized to a surface enable high-throughput experiments that require only small amounts of analyte. For example, protein "chips" can be used to detect protein-ligand, protein-protein, and antibody-antigen interaction. Attaching proteins or other chemical species covalently, rather than non-covalently produces more robust surfaces. Methods and reagents for immobilization that result in the formation of covalent and stable linkages provide significant benefit. Additionally, the ability to attach proteins or other chemical species to a surface in a uniform rather than random manner and which results in high-density attachment can provide a substantial advantage in assay sensitivity.

Protein microarrays [53, 54] facilitate high-throughput approaches for the discovery and characterization of protein-ligand interactions which are useful in the study of complicated biological pathways. Additionally, protein microarrays facilitate high-throughput methods of screening small molecule libraries as potential enzyme inhibitors and protein binding agents which are important in drug development. Moreover, protein microarrays provide recyclable devices that can be used to detect disease biomarkers in fluids of patients and are a great aid in disease diagnosis.

While DNA microarrays [55] have been produced in a large scale to study gene function, the fabrication of protein microarrays is more arduous. A major complicating factor is the tremendous chemical complexity of proteins. Proteins consist of 20 amino acids, each bearing a different side chain with distinct chemical properties, some of which possess further diversity as a result of post-translational modification. Moreover, the same amino acid exhibits different reactivity when present in different positions in a protein. In addition, proteins have limited stability and are susceptible to loss of activity when subjected to chemical modification. Accordingly, one of the major challenges in protein microarray technology is the development of general and facile strategies for protein immobilization.

Proteins have been immobilized on surfaces both non-covalently and covalently [56]. Facile, non-covalent immobilization has been achieved by physical adsorption [31, 57] and affinity tag mediated complex formation reactions [58, 59]. Nonetheless, covalent immobilization of proteins results in a more robust protein array.

Proteins are nucleophilic. Their side chains contain no electrophiles other than the disulfide bonds of cysteines or functional groups installed by post-translational modification. Accordingly, the chemical reactivity of proteins necessarily entails nucleophilic side chains, such as those of lysine [1] and cysteine [2,3]. The prevalence of these residues obviates control over the regiochemistry of reactions [4], producing heterogeneous reaction products often at the expense of biological function [3,5].

Covalent immobilization via nucleophilic side chains of lysine and cysteine residues [1, 60] produces a randomly oriented protein array. In contrast, site-specific covalent immobilization, either via an engineered cysteine [3] or via a non-proteinogenic group installed in a protein, affords a uniformly oriented protein array. Oriented protein arrays exhibit higher ligand binding ability [3, 61] and better reproducibility of enzymatic activity [62] when compared to arrays generated by random immobilization.

An intermediate that forms during the intein-mediated splicing of proteins contains an electrophile—a thioester (FIG. 1) [6]. The orthogonal reactivity of this functional group (as an electrophile) compared to the predominantly nucleophilic groups of proteins an be exploited for the site-specific modification of a protein by reaction with cysteine derivatives [7] or tandem reaction with a small-molecule thiol and amine [8]. Although thiols are potent nucleophiles for thioesters, the resultant thioesters are inherently unstable to hydrolysis [9], making the simple transthioesterification of an intein-derived thioester unsuitable for the chemical modification of proteins.

The powerful methods of native chemical ligation [10] and expressed protein ligation [11] offer an ingenious solution to this problem. After transthioesterification with a cysteine residue, S→N acyl transfer regenerates the thiol and forms a stable amide linkage. This approach, which has been used for protein modification and immobilization [12,13], however introduces a residual thiol that can be the focal point for undesirable side reactions. For example, cysteine is by far the most reactive residue toward disulfide bonds, $O_2(g)$, and other common electrophiles [14]. In addition, the sulfhydryl group of cysteine can undergo β-elimination to generate dehydroalanine [15], or disrupt self-assembled monolayers on gold or silver surfaces [16]. An alternative means to exploit intein-derived thioesters for the installation of an orthogonal functional group is needed in view of these detrimental attributes.

In contrast to sulfur nucleophiles, nitrogen nucleophiles could, in theory, react directly with the thioesters formed during intein-mediated protein splicing to form inert linkages. This reaction has been neither explored nor exploited previously. Additionally, reagents carrying a nitrogen nucleophile and a functional group exhibiting orthogonal reactivity (a hetero bifunctional reagent) could, again in theory, both attack an intein-derived thioester to form a stable linkage and install the orthogonal (and thus useful) functional group.

The azido group can serve in many applications as an orthogonal functional group, being absent from natural proteins, nucleic acids, and carbohydrates [17]. Moreover, chemical reactions of the azido group, such as the Cu(I)-catalyzed Huisgen 1,3-dipolar azide-alkyne cycloaddition [18] and Staudinger ligation [19] could be used for site-specific modification or immobilization. Azido-proteins have been produced previously. For example, Schultz and coworkers have developed a method for incorporating azidolysine into proteins [20]. Their approach involves producing a suppressor tRNA charged with azidolysine that inserts that residue into a protein as directed by an engineered gene. This method, although site-specific, is labor intensive and low yielding. Tirrell, Bertozzi, and coworkers have incorporated an azido group into a protein by using azidohomoalanine, which replaces methionine in proteins produced in methionine-depleted bacterial cultures [21]. This method is not site-specific for proteins containing more than one methionine residue.

U.S. Pat. No. 6,972,320 reports the coupling of peptides and proteins derivatized with azido groups with those derivatized with phosphinothioester groups via reaction of these functional groups to form an amide bond. U.S. patent application 2005/0048192 (Raines and Soellner) published Mar. 3, 2005 reports the use of azido functional groups for site-selective rapid and high-yielding covalent ligation of molecules, including peptides and proteins, to surfaces. The ligation is based on the reaction of an azide with a phosphinothioester to form an amide bond through which the molecule is immobilized on the surface.

Methods and reagents that would allow derivatization at thioesters formed in proteins, particularly those formed during intein-mediated splicing, where the resulting linkage is stable and which further allow incorporation of a functional group with orthogonal reactivity, such as an azide, for subsequent reaction would clearly be useful in the art.

SUMMARY OF THE INVENTION

This invention provides methods and reagents for site-selective functionalization of peptides and proteins. The method is based on the reaction of thioesters with hydrazine. The methods and reagents herein can be employed to covalently attach or link a peptide or protein, including protein fragments, to another chemical entity, which may be a functional group, a reporter molecule, label or tag, a biological molecule (e.g., a peptide, protein, carbohydrate, nucleoside or nucleic acid, or lipid), a ligand (for example, a steroid among many others) that in turn binds to a receptor (which may be a cell surface receptor), a variety of small molecules, e.g., drugs, drug candidates, antibiotics and the like, or a surface which most generally can be biological surface (e.g., a cell surface) or a substrate surface. The functionalization can be conducted in a physiological acceptable environment in aqueous buffer at pH near 7.0 (neutral pH) and at physiological temperatures which minimizes or avoids inactivation of biological molecules (e.g., peptides or proteins).

In specific embodiments the invention provides a method for linking a chemical entity or species to a target peptide or protein in which a peptide or protein having one or more thioester groups is reacted with a chemical species carrying a hydrazine group of the formula:

$H_2N-NH-CH_2-M-L-R$ and salts thereof wherein:

R is generally any chemical entity or species which is to be attached or covalently bonded to a protein or peptide; R can be a functional group, a reporter molecule, label or tag, a biological molecule (e.g., a peptide, protein, carbohydrate, nucleoside or nucleic acid, or lipid), a ligand (for example, a steroid among many others) that in turn binds to a receptor (which may be a cell surface receptor), a variety of small molecules, e.g., drugs, drug candidates, antibiotics and the like;

M is a single bond or a divalent chemical group carrying a non-bonding electron pair, such as $-C(O)NR'-$, where R' is H, or an alkylene or arylene group; and L is an optional linker group.

The L group can be any chemical species that provides a linker or spacer function which does not contain functional groups that react with hydrazine and preferably which does not contain functional groups that themselves react with the peptides or proteins that are to be functionalized or the chemical entities of the M and R group that is to be linked to the protein or peptide. The linker is a divalent chemical species which bonds between the M and R groups and which may carry functional groups which do not react with hydrazine, and which preferably do not react with the peptide or protein or the M or R groups, or functional groups which are protected (employing standard art-recognized protecting groups) against reaction with hydrazine, and preferably protected against reaction with the peptide or protein, and the M and R groups. In specific embodiments, where R is or comprises a functional group that exhibits orthogonal reactivity, such as an azido group, an alkenyl, an alkynyl, or a triazole group, L should not react with any of such orthogonal functional groups. The linking group preferably does not contain thiol groups, selenol groups, primary amine groups, alkoxyl amine groups ($H_2N-O-R$), hydroxamic acid groups, peroxide groups, aldehyde or ketone groups, unless the groups are protected with suitable protective groups which render them unreactive under conditions employed in the methods herein.

The linker is typically an organic species, having at least one carbon atom, which can include an alkylene chain, e.g., $-(CH_2)_n-$ where n is an integer indicating the length of the chain and wherein one or more carbons of the chain are optionally substituted with non-reactive or protected functional groups as described above. The organic linker may also be an alkylene chain in which one or more typically non-neighboring $CH_2$ groups are replaced with O, S, CO, an ester or amide group, or an $N(R'')_2$ group, wherein R'' is a hydrogen, an alkyl or an aryl group and at least one R'' is not hydrogen, the organic linker may be an arylene group (e.g., a phenylene [e.g., $-C_6H_5-$], biphenylene [e.g., $-C_6H_5-C_6H_5-$], or a divalent naphthylene group [e.g., a 1,5-naphthylene or a 1,4-naphthylene]), wherein one or more of the ring carbons are replaced with a heteroatom (O, N or S), or the organic linker may contain alkylene and arylene portions (e.g., $-CH_2-C_6H_5-$, or $-CH_2-C_6H_5-CH_2-$) wherein one or more typically non-neighboring $CH_2$ groups of the alkylene are replaced with O, S, CO, an ester or amide group, or an $N(R'')_2$ group, wherein R'' is a hydrogen, an alkyl or an aryl group and at least one R'' is not hydrogen and/or one or more of the arylene ring carbons are replaced with a heteroatom (e.g., O, N or S). In specific embodiments, L is an alkylene linker, an arylene linker or a polyether linker.

Linkers include those comprising ether groups, polyethers, alkyl, aryl (e.g., groups containing one or more phenyl rings) or alkenyl groups, or ethylene glycol groups. In certain embodiments, linkers can range in length from 2 to 1,000 atoms in length. In certain embodiments, linkers consist of 2 to 1,000 atoms. In additional embodiments, linkers consist of 2 to 50, 2-30, 2-20 or 2-10 atoms. A linker can be based on an alkylene chain in which one or more of the $CH_2$ groups of the chain is replaced with an O, S, NH, CO, or CONH group, where it is appreciated that dependent upon the application of the linker a CO group may need to be protected in the linker. A linker can be a substituted alkylene chain in which one or more carbons of the chain carries a non-hydrogen substituent, such as an OH, $NH_2$, or SH group or halide, where it is appreciated that dependent upon the application of the linker substituent group may need to be protected in the linker. A linker can be based on an divalent aryl group (arylene) in which one or more of the ring carbons are replaced with O, S, or N, where it is appreciated that dependent upon the application of the linker the arylene may need to be protected. A linker can be a substituted arylene in which one or more carbons of the group carries a non-hydrogen substituent, such as an OH, $NH_2$, or SH group or halide, where it is appreciated that dependent upon the application of the linker the substituent group may need to be protected in the linker.

Ether linkers include those of formula $-[(CH_2)r-O-(CH_2)s-O-]q-(CH_2)z$, where r, s, z and q are integers and z may also be zero, where r and s, r and z, s and z and r, s, and z may be the same or different. The integers r and s can range from 1-100, z can be 0 or be an integer ranging from 1-100 and q can range from 1-100. In specific embodiments, the integers r, s, and z can, for example range from 1-10 or 2-10, or 2-6 and q can, for example range from 1 to 100, 1-50, 1-20, 1-10 or 2-6.

A linker may be a polymer, such as a poly(ethyleneglycol). A linker typically may have residue moieties that remain after ligation of the linker via a functional group to a chemical species or a surface.

The linker may have discrete length where all molecules of the chemical species containing the linker have the same linker length (i.e., where in a $-(CH_2)$n-linker, n is a specific integer) or may be a polymeric linker in which the reagent comprises individual polymer molecules of different size, but which typically may be represented by an average number (n) of repeating units (RU), wherein L is $(RU)_n$, where n is the average number of repeating units.

In additional embodiments, L is a polymeric linker carrying polyethylene glycol chains, such as those that are comprised in Pegylation reagents, for example, polymethacrylates with polyethylene glycol chains such as those that are commercially available under the trade name POLY PEG (Trademark, Warwick Effect Polymers, UK). The average number of repeating units of a polymer is determined by measuring an average molecular weight of the polymer and dividing that average molecular weight by the weight of a repeating unit. Most typically the number average molecular weight is used to determine average number of repeating units. But as is well known in the art, average molecular weights of polymers can be measured or calculated in several different ways and will typically differ from one another as will the average number of repeating units calculated from them, because a given polymer is not monodisperse.

In certain specific embodiments, the linker is a polyether of formula $-(CH_2-CH_2-O)_p-CH_2-CH_2-$ where p is an integer ranging from 1-10 and more specifically n is 2, 3, 4 or 5 and which is not a polymeric polyether.

In specific embodiments, the reaction is carried out in aqueous buffer between pH 6-8 and more preferably at pH 7.

In specific embodiments, the chemical species carrying the hydrazine functional group is a hetero bifunctional reagent having the formula:

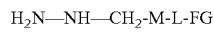

and salts thereof where:

M is a single bond or a chemical group carrying a non-bonding electron pair, such as $-C(O)NR'-$, where R' is H, or an alkyl or aryl group;

L is an optional linker group as described above; and

FG is a functional group having reactivity that is orthogonal to that of the hydrazine group, can be an azido, alkenyl, alkynyl, nitrile ($-CN$) or triazole group and is preferably an azido group ($-N_3$).

In certain embodiments, the hetero bifunctional reagent comprises an azido group and has the formula:

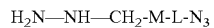

and salts thereof, where M and L are as defined above.

In more specific embodiments, the hetero bifunctional reagent has the formula:

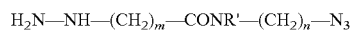

and salts thereof where m and n are, independently, integers ranging from 1-100, including 1-20, 1-10 and 1-6. In certain embodiments, m is 1 and n is 1-100, m is 1 and n is 1-20, m is 1 and n is 1-6, m is 1 and n is 2-6, m is 1 and n is 2, m is 3 and n is 1-100, m is 3 and n is 1-10, m is 3 and n is 2-6, m is 3 and n is 2, m is 1-3 and n is 1-3.

In other embodiments, the hetero bifunctional reagent has the formula:

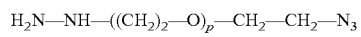

and salts thereof where p is or represents the number or average number of ether repeating units. The linker $((CH_2)_2-O)_p CH_2-CH_2$, which can also be written as -PEG- represents a polyethylene glycol spacer which may comprise a linker of discrete length where all molecules of the reagent have the same linker length (i.e., p is a specific integer) or a polymeric linker in which the reagent comprises individual polymer molecules of different size, but which typically may be represented by an average number of repeating units. In certain specific embodiments, the reagent is not a polymeric reagent and p is an integer ranging from 1-10 and more specifically p is 2, 3, 4 or 5. In certain embodiments, the reagents are polymers in which the linker is a polymeric material, such as a PEG.

In specific embodiments, the chemical species carrying the hydrazine group is immobilized on a surface. More specifically, the chemical species has formula:

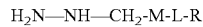

or salts thereof, where R comprises a surface. Hydrazine-functionalized surfaces can for example be prepared by reaction of the bifunctional reagent of formula:

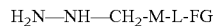

with a surface carrying one or more groups which react with FG to form a covalent bond. For example, when FG is an azido group, the bifunctional reagent is reacted with a surface which carries phosphinothiol groups to immobilize hydrazine to the surface.

In a specific aspect of the invention, intein-mediated protein splicing is employed to generate protein thioesters which can be reacted with hydrazine-containing chemical species or the hetero bifunctional reagents of this invention to covalently link the protein (or protein fragment) to various chemical species or to attach a functional group at the C terminus of the protein. The method is based on the capture of an intein-derived thioester with the hydrazine group. The method can be used for example to covalently link an azido group or other orthogonal reactive group to a protein. The covalently linked functional group can be used to further derivatize the protein, for example with a reporter molecule, label or tag or to link the protein to a surface. For example, a bifunctional reagent carrying a hydrazine and an azido group can be employed to covalently link an azido group to a protein without affecting the function of the protein.

An azido group covalently linked to a peptide or protein can be further reacted, for example, via a Huisgen 1,3-dipolar azide-alkyne cycloaddition, to attach a reporter molecule, label or tag, such as a fluorophore, to the peptide or protein or to immobilize the peptide or protein to a surface. An azido group attached at the C-terminus of a protein can also be used for site-specific protein immobilization which can be preferable to random immobilization, [3,5] and to modification by Staudinger ligation. [19] The method can also be employed to attach functional groups with orthogonal reactivity other than azido groups, for example, alkene, alkyne, triazole or nitrile groups to a target protein.

In specific embodiments, the invention provides a general method for producing proteins labeled site-specifically with an azido group. These azido-proteins can be produced by semisynthesis using a variation of expressed protein ligation (FIG. 1) [11]. The method involves producing the protein of interest as a fusion protein with an intein and a tag for affinity chromatography. On-resin cleavage of the intein-derived thioester is induced with a bifunctional reagent bearing a nucleophile for thioesters and an azido group, such as the bifunctional reagent above. This method is used to produce an azido-protein that maintains biological activity, preferably full biological activity, and displays at its C terminus an azido group that is available for chemoselective modification. Thus, exploiting the intrinsic and orthogonal reactivity of the thioester produced during intein-mediated protein splicing enables the site-specific chemical modification of a protein.

In a specific embodiment, azido-proteins are immobilized to a surface by reaction of the azido groups with functional groups on the surface, in particular with surface-attached phosphinothioester groups. The invention further provides surfaces to which one or more proteins (which may be the same or different proteins) are immobilized by reaction of an azido-protein with a surface attached phosphinothioester. More specifically, the invention provides surfaces immobilized with one or more proteins (or protein fragments) employing azido-proteins and methods described herein. The invention provides surfaces in which the immobilized proteins or protein fragments retain 50% or more of the activity of the free (non-immobilized) proteins or protein fragments. In more specific embodiments, immobilized proteins retain 75% or more or 90% or more of the activity of the free (non-immobilized) proteins or protein fragments.

In a specific embodiment, the azido-proteins formed by the methods of this invention can be employed to generate a microarray of a plurality of different peptides, and/or proteins.

The invention provides kits for carrying out the methods of this invention for functionalization of peptides and/or proteins, for ligation of peptides or proteins to various chemical species and/or for immobilization of functionalized peptides or proteins of this invention on to one or more surfaces. Such kits may comprise a carrier, such as a box, carton, tube or the like, adapted to receive one or more containers, such as vials, tubes, ampules, bottles and the like. Containers of the kit comprise selected amounts of one or more compounds, reagents, or buffers or solvents useful in carrying out a method of the invention.

In specific embodiments, a kit of this invention comprises one or more chemical species having a hydrazine group of this invention according to any of the chemical formulas herein. In more specific embodiments, a kit of this invention can comprise one or more chemical species which carry a hydrazine group and a reporter, label or tag for linking to a peptide or protein. Alternatively, a kit of this invention can contain starting materials, reagents, buffers or solvents for generating one or more hydrazine-containing species of this invention. In other specific embodiments, a kit of this invention can contain one or more bifunctional reagents of this invention which comprise a hydrazine group and a second functional group exhibiting orthogonal reactivity, particularly an azido group. More specifically, a kit of this invention can comprise one or more bifunctional reagents useful for immobilizing a peptide or protein to a surface.

Kits may further comprise one or more additional components necessary for carrying out one or more particular applications of the methods and reagents of the present invention. For example, the kit may comprise one or more chemical species which are to be ligated to a peptide or protein employing the methods and/or reagents of this invention. In a specific example the bifunctional reagent comprises a hydrazine group and an azido group and the kit comprises a chemical species which can be reacted with the azido group for attachment of the peptide or protein. The chemical species that is to be attached to the peptide or protein can include peptides, proteins, carbohydrates, lipids, nucleosides or nucleic acids or any of a variety of small molecules. In specific examples, the kits contain one or more labels, tags or reporter molecules for attachment to the peptide or protein. In another specific example, the kits contain a surface upon which the peptides or proteins can be immobilized. For example the kit may contain one or more components useful for the carrying out an assay employing a functionalized peptide or protein prepared using the bifunctional reagent. In general, kits may also contain one or more buffers, reaction containers or tools for carrying out the functionalization or other method, means for purification of functionalized peptides or proteins, control samples, one or more sets of instructions, and the like. In specific embodiments, kits can comprise reagents and starting materials for generating a peptide or protein carrying a thioester group for reaction with a hydrazine compound or reagent of this invention.

In a specific embodiment, the invention provides a kit which comprises reagents, buffers and one or more other components for forming a protein thioester by intein-mediated splicing. Such kits optionally include a surface upon which the protein thioester is formed for subsequent reaction with a hydrazine compound or reagent of this invention. Such kits can further comprise one or more hydrazine compounds or reagents of this invention, one or more buffers for carrying out a method of the invention, one or more surfaces for immobilization of functionalized proteins, one or more chemical species for attachment to functionalized proteins, one or more means for assaying functionalized proteins and instructions for carrying out one or more methods of this invention.

Other aspects of the invention are clear on consideration of the specification hereof including the drawings and non-limiting examples.

BRIEF DESCRIPTION OF THE DRAWINGS

FIG. 1 (a) shows visualization with Coomassie-blue staining and (b) shows visualization with fluorescence imaging.

DETAILED DESCRIPTION OF THE INVENTION

Figure 1:
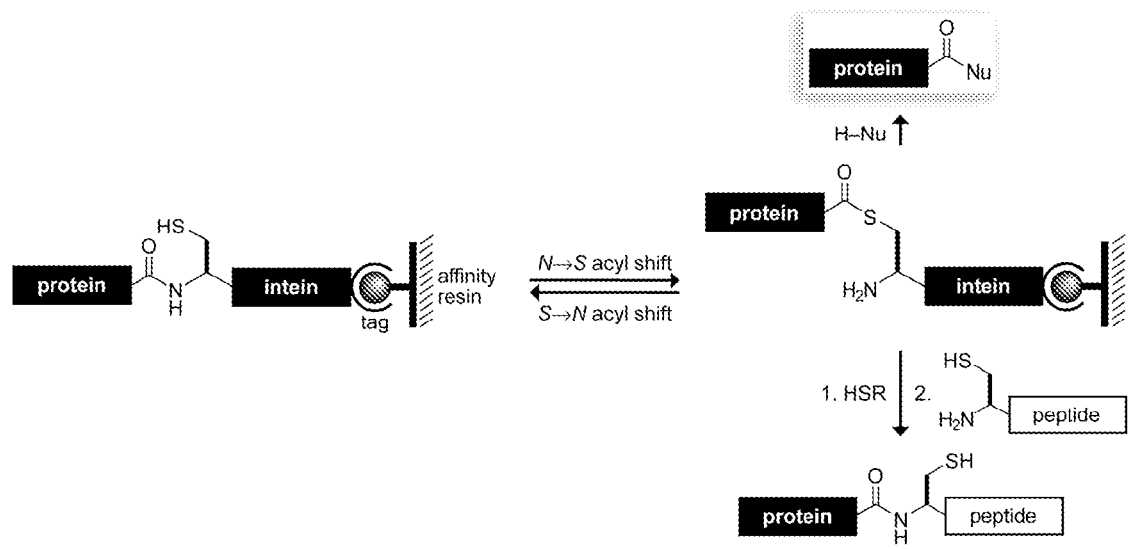
FIG. 1 illustrates the mechanism of expressed protein ligation [11] and on-resin capture of the thioester intermediate with a small-molecule nucleophile (H-Nu). The figure also shows the structure of the captured thioester when the nucleophile is hydrazine.
Figure 1:
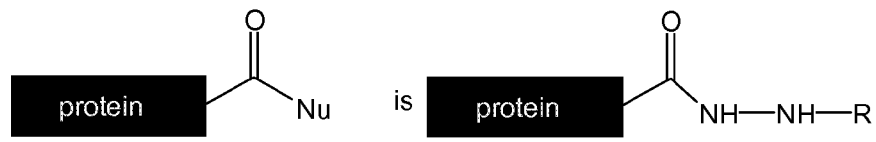

Most generally the invention relates to methods and reagents for covalent ligation of a peptide or protein which has one or more thioester groups (and preferably has a single thioester group, particularly at a C-terminus of the peptide or protein) to another chemical species by means of the reaction of a nucleophilic hydrazine group with the thioester of the peptide or protein.

Chemical species that can be covalently linked to a peptide or protein include other peptides or proteins, protein fragments, carbohydrates (e.g., saccharides), amino acids, lipids, nucleosides or nucleic acids, reporter molecules, tags or labels (e.g., a group whose presence can be detected by optical spectroscopy or mass spectrometry or other instrumental method), including a fluorescent or phosphorescent group (e.g., fluorescein and the like), an isotopic label or a radiolabel. Small molecules that can be ligated to a peptide or protein include amino acids, dipeptides, tripeptides, monosaccharides, disaccharides, reporter molecules, haptens that bind selectively to an antibody, ligands that bind to a receptor (such as one or more steroids), drugs or drug candidates, antibiotics and other small molecule therapeutics. The term chemical species is used broadly herein to refer to any chemical moiety to which a covalent bond can be formed. In specific embodiments, the chemical species is a surface or substrate to which the peptide or protein can be ligated. In a specific embodiment, the chemical species that is covalently linked to the peptide or protein is a chemical species other than a peptide or protein is a chemical species other than an amino acid.

It will be appreciated that covalent linking of the chemical species to the peptide or protein can proceed by reaction of a chemical precursor of the chemical species which carries a hydrazine group. The chemical precursor can be the species of formula:

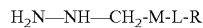

H$_2$N—NH—CH$_2$-M-L-R and salts thereof as defined above.

Alternatively, the covalent linking of the chemical species to the peptide or protein can proceed in two steps in which the peptide or protein is reacted with a bifunctional reagent of formula:

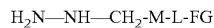

H$_2$N—NH—CH$_2$-M-L-FG and salts thereof as defined above to form an intermediate peptide or protein functionalized with an FG group:

peptide/protein-CO—NH—NH—CH$_2$-M-L-FG

FG is a functional group having reactivity that is orthogonal to that of the hydrazine group. In specific embodiments FG is an azido, alkenyl, alkynyl, nitrile (—CN) or triazole group and is preferably an azido group (—N$_3$). In a specific embodiment, FG is an azido group and the functionalized intermediate is an azido-functionalized peptide or protein. The intermediate FG functionalized peptide or protein can then be reacted with a precursor of the chemical species which reacts with FG to form a covalent linkage to the chemical species. For example, when FG is an azido group, the precursor of the chemical species can comprise a phosphinothioester or an alkynyl group which reacts with the azide to form an amide or a 1,3-dipolar azide-alkyne cycloaddition product, respectively.

In another alternative, the bifunctional reagent can first be reacted with a precursor to the chemical species that is to be ultimately covalently linked to the peptide or protein to form a chemical species functionalized with a hydrazine group, e.g.:

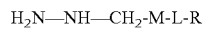

H$_2$N—NH—CH$_2$-M-L-R or a salt thereof, where R comprises the chemical species and any residual atoms or groups that remain after reaction of the FG with the precursor to the chemical species. The bifunctional reagent of this invention can for example be employed to generate a surface which is functionalized with hydrazine groups. For example, a bifunctional reagent where FG is an azido group can be reacted with a precursor of the chemical species which also carries a phosphinothiol group (forming an amide linkage to the chemical species) or with a precursor of the chemical species which also carries an alkynyl group (forming a cycloaddition product by 1,3-dipolar azide-alkyne cycloaddition). The intermediate species in this alternative is the chemical species that is hydrazine-functionalized. The chemical species may be any of those noted above and in particular can be a peptide, protein or a surface. The hydrazine-functionalized intermediate may for example be a hydrazine-functionalized peptide or protein or a hydrazine-functionalized surface. The hydrazine functionalized intermediate can then be reacted with a peptide or protein which carries one or more thioester groups to form a covalent linkage between the peptide or protein and the chemical species.

It will be appreciated that the bifunctional reagents of this invention and in particular those in which FG is an azido group can be useful in general for forming a covalent linkage between two chemical species, wherein one of the chemical species carries a thioester group or is functionalized to carry a thioester group which reacts with the hydrazine group and wherein the other chemical species carries a functional group or is functionalized to carry a functional group which reacts with the FG group. When FG is an azido group, the chemical species, for example, carries a phosphinothiol group or an alkynyl group which each react with an azido group. In a specific embodiment, the bifunctional reagent can be used to covalently link a chemical species carrying a thioester group (most generally called a thioester) and a chemical species carrying a phosphinothiol group (most generally called a phosphinothiol). In another specific embodiment, the bifunctional reagent can be employed to covalently link a thioester to a an alkyne (chemical species carrying an alkynyl group).

In general any peptide or protein can be functionalized or immobilized employing the methods and reagents herein. The term peptide is used broadly herein to refer to small peptides and polypeptides. For improved clarity we designate small peptides as those having from 2-100 amino acids and polypeptides as peptides having more than 100 amino acids. Peptides which can be functionalized include small peptides having 2 to 100, 2 to 50, 10-100 and 10-50 amino acids and include polypeptides having 100 or more amino acids or 200 or more amino acids. Polypeptides in some cases may be proteins.

Proteins include among others, enzymes, receptors, antibodies and antibody fragments. In general, any peptide or protein can be functionalized or ligated to a surface employing the inventive method. Useful peptides and proteins can be synthetic, semi-synthetic and biosynthetic. In particular, peptides or proteins can be synthesized using solid-phase peptide synthesis or related methods. Peptides and proteins can be isolated from natural sources (e.g., isolated from a bacterial, plant or animal source) or prepared by recombinant methods (e.g., by expression in a recombinant host). Proteins include among others glycoproteins, lipoproteins, fusion proteins, enzymes, receptors, antibodies, and antibody fragments. Proteins may be monomers, homodimers, heterodimers, and aggregates containing a plurality of polypeptides. Proteins and protein fragments include libraries of proteins and/or protein fragment variants in which the individual variants different from one another in size or structure, amino acid sequence, or derivatization. Proteins and protein fragment libraries can include libraries containing a plurality of mutant proteins in which one or more amino acids of a polypeptide sequence of the protein or protein fragment are altered from a naturally-occurring (e.g., wild-type) protein sequence.

In general, the thioester group of the peptide or protein can be formed on either terminus or on an amino acid side group by methods that are known in the art. Preferably the peptide or protein carries a single thioester group for selective reaction with a hydrazine compound or reagent. Preferably the thioester group is at the C-terminus of the peptide or protein and in a specific embodiment the thioester is formed by intein-mediated splicing.

In specific embodiments, peptides and proteins which are functionalized using the methods and reagents herein with an azido group can be immobilized to any surface that can be derivatized with phosphinothioester group. In particular, any molecule that has an azido functional group can be attached to a surface that is derivatized with a phosphinothioester, as long as the molecule and the surface, including surfaces of particulates, are compatible with the chemistry employed.

Additionally, azido functionalized peptides and proteins formed by the methods of this invention can be reacted with a alkyne functional group via a Huisgen 1,3-dipolar azide-alkyne cycloaddition to form a 1,2,3-triazole. Analogously, alkyne-functionalized peptides or proteins can be reacted with an azido functional group via the same cycloaddition.

In a specific embodiment, a protein thioester is first functionalized with an azido group by reaction with a bifunctional reagent carrying a hydrazine group and an azido group. The hydrazine reacts with the thioester to form a covalent linkage to the protein and functionalize the protein with the azido group. In a subsequent step, the azido protein is reacted with a phosphinothioester in a modified Staudinger reaction to form an amide bond to covalently attach or ligate the protein to a surface. In general, any azide (a molecule containing an azido group) can be ligated to a phosphinothioester derivatized surface as has been described in U.S. patent application 2005/0048192 (Raines and Soellner) published Mar. 3, 2005.

Immobilization of a protein to a surface employing a bifunctional reagent of this invention is illustrated in Scheme 1:

Scheme 1: Use of bifunctional reagent to immobilize proteins to a surface functionalized with phosphinothioesters:

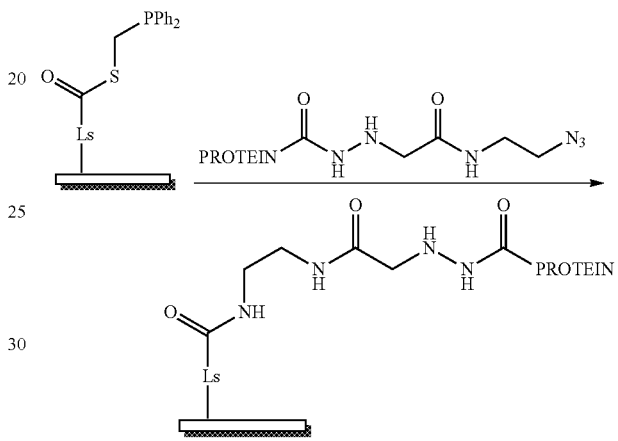

where Ls is a covalent linkage to the surface which can generally be an alkylene chain, $-(CH_2)_s-$, where s is an integer indicating the length of the chain) wherein one or more $-CH_2-$ groups can be replaced with a $-N-$, $-O-$, $-S-$, $-NH-$ or CO atom or group. Specific Ls groups include, among others: $-(CH_2)_{s1}-NH-CO-(CH_2)_{s2}-$, $-(CH_2)_{s1}-CO-NH-(CH_2)_{s2}-$, $-(CH_2)_{s1}-NH-CO-(CH_2)_{s2}-X-(CH_2)_{s3}-$, $-(CH_2)_{s1}-CO-NH-(CH_2)_{s2}-X-(CH_2)_{s3}-$, where X is an ether or polyether group including a PEG and where s1, s2 and s3 are integers. In specific embodiments, s is an integer ranging from 1-100, 2-100 or 2-50. In more specific embodiments, s is an integer ranging from 2-10. In specific embodiments, s1, s2 and s3 are integers ranging from 1-100, 2-100 or 2-50. In a specific embodiment, s1+s2+s3 ranges from 4-100, 6-100 or 6-50. In more specific embodiments, s1, s2 and s3 are integers ranging from 2-10.

A phosphinothioester useful in this ligation can be generated in a number of ways. For example, an activated carboxylic acid derivative, e.g., a thioester or a N-acylsulfonamide, can be converted into a phosphinothioester. Any method known in the art for forming a phosphinothioester can in general be used. Published PCT application US/01/087920 provides an efficient method for generating phosphinothioesters, particularly those of amino acids, peptides and protein fragments using a phosphinothiol reagent. Phosphinothiol reagents can also be employed, as described in U.S. patent application 2005/0048192 to provide surfaces derivatized with phosphinothioesters. The phosphinothiol reagent can be used to generate the desired phosphinothioester from activated carboxylic acid derivatives (e.g., which are activated for nucleophilic attach such as thioesters or activated sulfamyl groups) or from a carboxylic acid by conventional coupling reactions mediated by dicyclohexylcarbodiimide or a similar coupling.

A phosphinothioester useful in the ligation reaction of this invention can also be generated from a peptide or protein fragment that is attached to a resin at its C-terminus. For example, a peptide or protein fragment can be released from a resin by reaction with a phosphinothiol reagent of this invention to generate a phosphinothioester. A peptide or protein fragment can be synthesized on an appropriate resin using known methods of solid state peptide synthesis, e.g., Fmoc-based methods. The peptide or protein fragment synthesized on the resin can then be released by reaction with a phosphinothiol to generate a phosphinothioester which then can be ligated with an azide to form an amide bond. In this aspect of the invention, any resin known in the art to be appropriate for peptide synthesis and that is compatible for reaction with a phosphinothiol to generate a phosphinothiol ester can be employed in this invention. Resins known in the art as "safety-catch" resins are of particular interest [85].

In a specific embodiment, the invention provides a surface to which one or more peptides, proteins or both are covalently immobilized through a chemical linkage which comprises the chemical group:

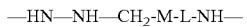
—HN—NH—CH$_2$-M-L-NH— wherein M is a single bond or a chemical group carrying a non-bonding electron pair, and L is an optional linker group which if present is an alkylene chain —(CH$_2$)$_n$— where n is an integer indicating the length of the chain, wherein one or more carbons of the chain are optionally substituted with a non-reactive or protected functional group which does not react with hydrazine and wherein one or more non-neighboring CH$_2$ groups are replaced with O, S, CO, an ester or amide group, an arylene group, or an N(R")$_2$ group, wherein R" is a hydrogen, an alkyl or an aryl group and at least one R" is not hydrogen. Such surfaces can be prepared employing a bifunctional reagent of this invention. A plurality of peptides, proteins or both can be immobilized to a surface or a plurality of surfaces to form a microarray.

More specifically, the invention provides a surface to which one or more peptides, proteins or both are covalently immobilized through a chemical linkage which comprises the chemical group:

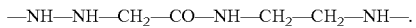
—NH—NH—CH$_2$—CO—NH—CH$_2$—CH$_2$—NH—.

Such surfaces can be prepared employing a bifunctional reagent of this invention. A plurality of peptides, proteins or both can be immobilized to a surface or a plurality of surfaces to form a microarray.

In a specific embodiment, the invention provides a method for covalently attaching one or more proteins to one or more surfaces wherein immobilized yields of equal to or greater than 50% are obtained.

Surfaces that can be used in this invention include, but are not limited to glass (including glass slides), quartz (including optical fibers), various metal surfaces such as gold with thiol monolayers (in particular BIAcore), colloidal gold, semiconductors, diamond, silicon, plastic, ceramics, alum, hydroxyapatite, polyacrylamide, polyimines, polypropylene, latex, rubber, agarose, chitin, chitosan, dextran and derivatized dextrans, cellulose and derivatized cellulose (e.g., nitrocellulose, cellulose acetate), nylon, polyvinyl chloride, and polystyrene (resins, etc), artificial bone material. Surfaces can be flat or curved and can be a film, a plate, a fiber, plate wells, a wafer, a grid, a mesh, a membrane, beads or pins. Surfaces can be rigid or pliable, or the surface of a gel. Surfaces may further be composed of a plurality of solid particles, resins or beads. Surfaces having an immobilized amino acid, peptide, protein fragment, protein, carbohydrate, lipid, nucleoside, nucleotide, nucleic acid, or small molecule attached can be part of an array, such as multi-well plates or a microarray on a flat surface. Surfaces which are derivatized, for example to carry amine, OH, epoxy, carboxylate or ester surfaces are commercially available or can be prepared by well-known techniques.

Typically, the peptides and proteins are covalently attached to a selected chemical species through a linker group which can act as a spacer between the peptide/protein and the chemical species. Linker groups are generally selected for compatibility with the ligation chemistry and for compatibility with the application of the resulting functionalized or immobilized peptide or protein. Linker groups can have various chemical structures as discussed above and preferably do not carry functional groups or have structures that interfere with the reactivity of the hydrazine group or any other linked functional groups. The linker further should not react with the peptide or protein and should not detrimentally affect the activity of the peptide or protein or other chemical species to which it is attached. Carbon atoms of the linker may be substituted with functional groups which do not react with or which carry protective groups which prevent their reaction with the hydrazine, azido or other orthogonal functional group that function in a method of this invention (including additional useful orthogonal functional groups such as alkene, alkyne, triazole or nitrile groups).

The term "alkyl" refers to a monoradical of a branched or unbranched (straight-chain or linear) saturated hydrocarbon and to cycloalkyl groups having one or more rings. Unless otherwise indicated preferred alkyl groups have 1 to 30 carbon atoms and more preferred are those that contain 1-22 carbon atoms. Short alkyl groups are those having 1 to 6 carbon atoms including methyl, ethyl, propyl, butyl, pentyl and hexyl groups, including all isomers thereof. Long alkyl groups are those having 8-30 carbon atoms and preferably those having 12-22 carbon atoms as well as those having 12-20 and those having 16-18 carbon atoms. The term "cycloalkyl" refers to cyclic alkyl groups having preferably 3 to 30 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantanyl, and the like.

The term "alkenyl" refers to a monoradical of a branched or unbranched unsaturated hydrocarbon group and to cycloalkenyl groups having one or more rings wherein at least one ring contains a double bond. Unless otherwise indicated preferred alkenyl groups have 2 to 30 carbon atoms and more preferred are those that contain 2-22 carbon atoms. Alkenyl groups may contain one or more double bonds (C=C) which may be conjugated or unconjugated. Preferred alkenyl groups are those having 1 or 2 double bonds and include omega-alkenyl groups. Short alkenyl groups are those having 2 to 6 carbon atoms including ethylene (vinyl), propylene, butylene, pentylene and hexylene groups, including all isomers thereof. Long alkenyl groups are those having 8-30 carbon atoms and preferably those having 12-22 carbon atoms as well as those having 12-20 carbon atoms and those having 16-18 carbon atoms. The term "cycloalkenyl" refers to cyclic alkenyl groups of from 3 to 30 carbon atoms having a single cyclic ring or multiple condensed rings in which at least one ring contains a double bond (C=C). Cycloalkenyl groups include, by way of example, single ring structures such as cyclopropenyl, cyclobutenyl, cyclopentenyl, cyclooctenyl, cylcooctadienyl and cyclooctatrienyl.

The term "alkynyl" refers to a monoradical of an unsaturated hydrocarbon having one or more triple bonds (C≡C). Unless otherwise indicated preferred alkynyl groups have 2 to 30 carbon atoms and more preferred are those that contain 2-22 carbon atoms. Alkynyl groups include ethynyl, propargyl, and the like. Short alkynyl groups are those having 2 to 6 carbon atoms, including all isomers thereof. Long alkynyl groups are those having 8-22 carbon atoms and preferably those having 12-22 carbon atoms as well as those having 12-20 carbon atoms and those having 16-18 carbon atoms. Preferred alkynyl groups have one triple bond and include those alkynyl groups with an ω (or terminal triple bond, e.g., CH≡CH—$(CH_2)_n$— where n is 0 or an integer, e.g., n=0 or 1-28).

The term alkoxy (or alkoxide) refers to a —O-alkyl group, where alkyl groups are as defined above. The term alkeneoxy (alkenoxide) refers to a —O-alkenyl group where alkenyl groups are as defined above and wherein a double bond is preferably not positioned at the carbon bonded to the oxygen. The term alkynoxy (alkynoxide) refers to a —O-alkynyl group where alkynyl groups are as defined above and wherein a triple bond is not positioned at the carbon bonded to the oxygen.

The term "alkoxyalkyl" refers to an alkyl group in which one or more —$CH_2$— groups are replaced with —O—. The term is synonymous with the term ether group and includes polyether groups (such as PEG). Unless otherwise specified preferred non-polymeric alkoxyalkyl groups have from 3 to 30 carbon atoms and more preferably have 6 to 22 carbon atoms. Ether groups include groups of the formula: —$[(CH_2)_a$—O—$]_b$—$CH_3$ where a is 1-10 and b is 1-6. More specifically, a can be 2, 3 or 4 and b can be 1, 2 or 3. The term "thioether group" or "thioalkoxyalkyl" refers to an alkyl group in which one or more —$CH_2$— groups are replaced with —S—. Unless otherwise specified, preferred thioalkoxyalkyl groups have from 3 to 30 carbon atoms and more preferably have 6 to 22 carbon atoms. Thioalkoxylalkyl groups include groups of the formula: —$[(CH_2)_a$—S—$]_b$—$CH_3$ where a is 1-10 and b is 1-6. The term thioether also includes "dithioalkoxyalkyl" groups which refers to an alkyl group in which one or more —$CH_2$— groups are replaced with —S—S-(or two adjacent —$CH_2$— groups are each replaced with —S—). Unless otherwise specified preferred dithioalkoxyalkyl groups have from 3 to 30 carbon atoms and more preferably have 3 to 22 carbon atoms. Dithioalkoxylalkyl groups include groups of the formula: —$(CH_2)_a$—S—S—$(CH_2)_b$—$CH_3$, where a can be 1-15 and b is 0-25. Alkoxyalkyl, thioalkoxyalkyl and dithioalkoxyalkyl groups can be branched by substitution of one or more carbons of the group with alkyl groups.

The term "alkylene" refers to a diradical of a branched or unbranched saturated hydrocarbon chain. Preferred alkylene groups have 1-30 carbon atoms, unless otherwise indicated and in particular can have 1 to 10 carbon atoms, or 1-6 carbon atoms, or 2-4 carbon atoms. This term is exemplified by groups such as methylene (—$CH_2$—), ethylene (—$CH_2CH_2$—), more generally —$(CH_2)_n$—, where n is 1-30, 1-20 or 1-10 or more preferably 1-6 or n is 2, 3 or 4. In embodiments of this invention n can be significantly larger than 30, e.g., ranging from 1, 2 or 3 to 100-200 or 300. Alkylene groups may be branched, e.g., by substitution with alkyl group substituents. Alkylene groups may be optionally substituted as described herein. Alkylene groups may have up to two non-hydrogen substituents per carbon atoms. Preferred substituted alkylene groups have 1, 2, 3 or 4 non-hydrogen substituents. Hydroxyl-substituted alkylene groups are those substituted with one or more OH groups.

The term "aryl" refers to a group containing an unsaturated aromatic carbocyclic group of from 6 to 22 carbon atoms having a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Aryls include phenyl, naphthyl and the like. Aryl groups may contain portions that are alkyl, alkenyl or akynyl in addition to the unsaturated aromatic ring(s). The term "alkaryl" refers to the aryl groups containing alkyl portions, i.e., -alkylene-aryl and -substituted alkylene-aryl. Such alkaryl groups are exemplified by benzyl, phenethyl and the like.

The term "arylene" refers to the diradical derived from an aryl group (including substituted aryl) as defined above and is exemplified by 1,2-phenylene, 1,3-phenylene, 1,4-phenylene, 1,2-naphthylene, 1,7-naphthylene, 1,5-naphthylene, and the like.

Most generally the terms aryl and arylene include heteroaryl and heteroarylene groups. The term "heteroaryl" refers to an aromatic group of from 2 to 30 (including 2-22) carbon atoms having 1 to 4 heteroatoms selected from oxygen, nitrogen and sulfur within at least one ring (if there is more than one ring). Heteroaryl groups may be optionally substituted. The term "heteroarylene" refers to the diradical derived from a heteroaryl (including substituted heteroaryl) groups as defined above.

The term "alkoxyalkylene" refers to a diradical of a branched or unbranched saturated hydrocarbon chain in which one or more —$CH_2$— groups are replaced with —O—, which unless otherwise indicated can have 1 to 10 carbon atoms, or 1-6 carbon atoms, or 2-4 carbon atoms. This term is synonymous with the term ether linker group and includes polyether linker groups, and further includes PEG linker groups. This term is exemplified by groups such as —$CH_2OCH_2$—, —$CH_2CH_2OCH_2CH_2$—, —$CH_2CH_2OCH_2CH_2OCH_2CH_2$— and more generally —$[(CR''_2)_a$—O—$]_b$—$(CR''_2)_c$, where R'' is hydrogen or alkyl, a is 1-10, b is 1-6 and c is 1-10 or more preferably a and c are 1-4 and b is 1-3. In specific embodiments herein n can be significantly larger than 10, ranging from 1, 2 or 3 up to several hundred or several thousand. Polymeric ether linkages can be used in reagents and compounds of this invention where n represent an average number of ether repeating units. Alkoxyalkylene groups may be branched, e.g, by substitution with alkyl group substituents. The term "thioalkoxyalkylene" refers to a diradical of a branched or unbranched saturated hydrocarbon chain in which one or more —$CH_2$— groups are replaced with —S—, which unless otherwise indicated can have 1 to 10 carbon atoms, or 1-6 carbon atoms, or 2-4 carbon atoms. This term is synonymous with the term thioether linker and includes polythioethers linkers. This term is exemplified by groups such as —$CH_2SCH_2$—, —$CH_2CH_2SCH_2CH_2$—, —$CH_2CH_2SCH_2CH_2SCH_2CH_2$— and more generally —$[(CR''_2)_a$—S—$]_b$—$(CR''_2)_c$, where R'' is hydrogen or alkyl, a is 1-10, b is 1-6 and c is 1-10 or more preferably a and c are 1-4 and b is 1-3. Thioalkoxyalkylene groups may be branched, e.g., by substitution with alkyl group substituents. The term "dithioalkoxyalkylene" refers to a diradical of a branched or unbranched saturated hydrocarbon chain in which one or more —$CH_2$— groups are replaced with —S—S—, which unless otherwise indicated can have 1 to 10 carbon atoms, or 1-6 carbon atoms, or 2-4 carbon atoms. Thioether linkers of this invention can be significantly longer than n=10, n can range from 1, 2 or 3 up to 100, 200 or 300, for example. This term is exemplified by groups such as —$CH_2S$—$SCH_2$—, —$CH_2CH_2S$—$SCH_2CH_2$—, —$CH_2CH_2CH_2$—S—S—$CH_2CH_2CH_2$— and more generally —(CR″$_2$)$_a$—S—S—(CR″$_2$)$_c$, where R″ is hydrogen or alkyl, a is 1-15, and c is 1-15 or more preferably a and c are 1-6. Dithioalkoxyalkylene groups may be branched, e.g., by substitution with alkyl group substituents. Preferable dithioalkoxyalkylene groups have one —S—S— group.

The term "amino" refers to the group —NH$_2$ or to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen. Unless otherwise indicated, Alkyl groups, alkenyl groups, alkynyl groups, aryl groups and carbons of alkenylene groups herein can be optionally substituted with one or more amino groups, and particularly with amine groups other than primary amine groups.

Haloalkyl refers to an alkyl group as defined herein substituted by one or more halides (e.g., F—, Cl—, I—, Br—) as defined herein, which may be the same or different. A haloalkyl group may, for example, contain 1-10 halide substituents. Representative haloalkyl groups include, by way of example, trifluoromethyl, 3-fluorododecyl, 12,12,12-trifluorododecyl, 2-bromooctyl, 3-bromo-6-chloroheptyl, and the like. Haloalkyl groups include fluoroalkyl groups. Alkyl groups, alkenyl groups, alkynyl groups, aryl groups and carbons of alkenylene groups herein can be optionally substituted with one or more halides and/or haloalkyl groups.

The terms alkyl, alkenyl, alkynyl, aryl, alkylene, and arylene groups as used herein refer to both substituted and unsubstituted groups. Alkyl, alkenyl, alkynyl, aryl, alkylene, and arylene groups may be optionally substituted as described herein and may contain non-hydrogen substituents dependent upon the number of carbon atoms in the group and the degree of unsaturation of the group. Unless otherwise indicated substituted alkyl, alkenyl, alkynyl, aryl, alkylene, and arylene groups preferably contain 1-10, and more preferably 1-6, and more preferably 1, 2 or 3 non-hydrogen substituents. Halogens are optional substituents of functional groups described herein and include fluorine, chlorine, bromine and iodine. A preferred halogen is fluorine. Substituted alkyl, alkenyl, alkynyl and aryl groups include haloalkyl, haloalkenyl, haloalkynyl, and haloaryl groups as well as perhalogenated alkyl, alkenyl, alkynyl, and aryl groups. Substituted alkyl, alkenyl, alkynyl and aryl groups include fluoroalkyl fluoroalkenyl, fluoroalkynyl and fluoraryl groups as well as perfluorinated alkyl, alkenyl, alkynyl and aryl groups. Specific halogenated substituents include trifluoromethyl groups, pentafluoroethyl groups, and pentafluorphenyl groups among others.

Unless otherwise stated, OH groups, alkoxy groups, thiol groups, thialkoxy groups, nitro groups (NO$_2$—), cyano (NC—), isocyano (CN—), thiocyano (NCS—), isothiocyano (SCN—), sulfuryl (SO$_2$—) are other optional substituents of groups described herein. Alkyl, alkenyl, alkynyl, aryl, alkylene and arylene groups may be substituted with one or more of these substituents. Dependent upon the application, it may be necessary to protect one or more of these substituents.

Those of ordinary skill in the art can readily select appropriate protecting groups based on what is generally known in the art for a given application. In specific embodiments, alkyl groups are substituted with 1-10 substituent groups (dependent in part on the number of carbon atoms in the alkyl group. In specific embodiments, alkyl groups having 1-20 or 1-10 carbon atoms are substituted with 1-3 substituent groups. In specific embodiments phenyl groups may be substituted with 1, 2, 3, 4 or 5 substituent groups. In a specific embodiment, alkyl groups are substituted with 1 or 2 of these substituent groups. In a specific embodiment, phenyl rings have a single substituent group (e.g., a hydroxy, alkoxy, thiol, thioalkoxy, nitro, cyano, isocyano, thiocyano, isothiocyano, or sulfuryl). In other specific embodiments, phenyl rings have two substituent groups.

As to any of the above groups which contain one or more substituents, it is understood, that such groups do not contain any substitutents or substitution patterns which are sterically impractical and/or synthetically non-feasible. In addition, the compounds of this invention include all stereochemical isomers arising from the substitution of the groups and compounds noted above.

In general any anions can be employed in the formation of salts of this invention. Acceptable anions include halides, sulfate, carboxylates, acetates, phosphate, nitrate, trifluoroacetate, glycolate, pyruvate, oxalate, malate, succinicate, acid, fumarate, tartarate, citrate, benzoate, methanesulfonate, ethanesulfonate, p-toluenesulfonate, salicylate and the like. For certain applications pharmaceutically acceptable salts, which are recognized in the art, may be preferred.

In this application the terms "orthogonal" or "orthogonal reactivity" relate generally to the relative reactivity of functional groups under selected reaction conditions (solvent, pH, temperature, etc.) One functional group has reactivity that is orthogonal to that of a second functional group, when the first functional group does not exhibit any measurable reactivity under conditions when the second functional group does react typically with respect to the same reactant or reaction and under the same reaction conditions. It will be appreciated that two groups may be orthogonal only under certain reaction conditions.

More specifically, the terms are used to define functional groups that are appropriate for use in chemical species and reagents of this invention which contain hydrazine groups. The hydrazine groups in the chemical species and reagents of this invention are intended to selectively react with thioester groups, particularly those in proteins and peptides, under certain conditions (particularly in aqueous or wet solvents at about pH 7 at physiologically acceptable temperatures.) Preferred functional groups that exhibit reactivity orthogonal to hydrazine groups are those which do not react with thioesters under the selected conditions used for functionalization of proteins and peptides with the hydrazine-containing species of this invention.

Bifunctional reagents herein contain a hydrazine group and a second reactive functional group exhibiting orthogonal reactivity to that of the hydrazine group. The second functional group is intended to provide for ligation to additional chemical species, for example, for immobilization to surfaces. Exemplary second functional groups are azido, alkenyl, alkynyl, nitrile and tetrazole groups. Bifunctional reagents herein preferably contain only those functional groups which exhibit reactivity orthogonal to hydrazine and the second functional group (under the reaction conditions selected for use in the methods herein). It is preferred that the compounds and reagents of this invention which are employed for functionalization of peptides and proteins do not contain functional groups, other than hydrazine and the second reactive functional group, if present, that themselves react with the peptide or protein.

Functional groups that may exhibit undesired reactivity can be protected with appropriate protecting groups as is known in the art. A large amount of information is known in the art concerning the use of protecting groups. One of ordinary skill in the art will be aware of this information and will be capable of selecting appropriate protecting groups for a given application. Further, if necessary, methods for determining whether or not a given protecting group will function for a given application under selected reaction conditions are known and available in the art and such determinations can be accomplished by routine experimentation.

While it is preferred that orthogonal functional groups do not exhibit any measurable level of reactivity with the thioesters herein under the selected conditions for functionalization relatively low amounts of undesired reaction may occur without significant detriment to the methods herein. A functional group which may show such insignificant low levels of undesired reactivity is described herein as "substantially orthogonal."

A large amount of information is known in the art concerning the relative reactivity of different functional groups. One of ordinary skill in the art of organic and bioorganic chemistry will be aware of this information and be capable of choosing functional group that generally exhibit desired reactivity (or do not exhibit undesired reactivity.) Further, methods for determining the relative reactivity of different functional groups under selected reaction conditions are known and available in the art and such relative reactivity can be assessed by routine experimentation.

Compounds and reagents of this invention can be prepared in view of the specific descriptions provided herein and what is known in the art or by routine adaptation of such methods in view of the disclosures herein.

The compounds of this invention may contain one or more chiral centers. Accordingly, this invention is intended to include racemic mixtures, diastereomers, enantiomers and mixture enriched in one or more stereoisomer. The scope of the invention as described and claimed encompasses the racemic forms of the compounds as well as the individual enantiomers and non-racemic mixtures thereof.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure.

A number of specific groups of variable definitions have been described herein. It is intended that all combinations and subcombinations of the specific groups of variable definitions are individually included in this disclosure. When a compound is described herein such that a particular isomer, enantiomer or diastereomer of the compound is not specified, for example, in a formula or in a chemical name, that description is intended to include each isomers and enantiomer of the compound described individual or in any combination.

Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein, the broad term "comprising" is intended to encompass and provide support for the terms "consisting essentially of" and "consisting of." The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional nucleic acids, chemically modified nucleic acids, additional cells, and additional uses of the invention.

THE EXAMPLES

Example 1

Identification of the Optimal Nucleophile for Thioesters

To identify the optimal nitrogen nucleophile for a thioester, kinetic studies were performed on a model chromogenic thioester: $AcGlySC_6H_4$-p-$NO_2$. The rate of release of the thiophenolate anion was monitored by measuring the change in absorbance at 410 nm (Scheme 1). Nitrogen nucleophiles with conjugate-acid $pK_a$ values ranging from 4.6 to 10.6 (Table 1) were used in the experiments. The logarithmic values of the second-order rate constants ($k_2$) of the unprotonated primary amines were plotted against the $pK_a$ values of their conjugate acids to yield the Brønsted plot shown in FIG. 2A. The data were fitted to the equation[26]:

$$\log k_2 = \log(AB) + (\beta + \beta')pK_a - \log(A10^{\beta pK_a} + B10^{\beta' pK_a}) \quad (1)$$

In eq 1, A and B are constants, $\beta'$ is the slope of the former part of the Brønsted plot, and $\beta$ is the slope of the latter part.

TABLE 1

| Nucleophiles used in this study and the $pK_a$ values of their conjugate acids. | |
|---|---|
| Nucleophile | $pK_a$ |
| $CH_3ONH_2$ | 4.60[22] |
| $F_3CCH_2NH_2$ | 5.40[23] |
| $C_2H_5O(O)CCH_2NHNH_2$ | 6.45[24] |
| $CH_3O(O)CCH_2NH_2$ | 7.75[22] |
| $CH_3NHNH_2$ | 7.87[25] |
| $FCH_2CH_2NH_2$ | 9.19[23] |
| $HOCH_2CH_2NH_2$ | 9.50[22] |
| $CH_3CH_2NH_2$ | 10.63[22] |

The Brønsted plot in FIG. 2a is biphasic. The slope changes from 0.81 with nucleophiles of low pKa to 0.42 with nucleophiles of high pKa. This change is due to the known change in rate-determining step from the formation of a tetrahedral zwitterionic intermediate to the decomposition of the intermediate into products [26-28]. The value of the slope obtained ($\beta'=0.81$) is in agreement with that for the aminolysis of oxygen esters [29]. As expected [30], "α-effect" nucleophiles (alkoxy amines, α-hydrazino acetyl, and alkyl hydrazine) exhibit much greater nucleophilicity than that predicted from their pKa values. In water, the α-effect could arise from the nucleophile being less solvated and hence more reactive because of the inductive withdrawal of electrons by the adjacent heteroatom [31].

The Brønsted plot reports on the nucleophilicity of unprotonated (that is, neutral) amines. According to FIG. 2a, the best nucleophile for thioesters in an environment in which all the amines are deprotonated is ethyl amine. Indeed, other simple amines have been used in tandem with a small-molecule thiol to modify an intein-derived thioester [8]. At the high pH necessary to deprotonate an amine, however, thioesters are prone to undergo hydrolysis [9]. Moreover, proteins are subject to unfolding and subsequent aggregation at high pH values [32]. Performing the reaction at pH 7.0 provides an acceptable trade-off between deprotonation of the nitrogen nucleophile and hydrolysis of the thioester. Data on the first-order rate constant (k1) for the reaction of various nitrogen nucleophiles at pH 7.0 under pseudo-unimolecular reaction conditions are shown in FIG. 2b. At pH 7.0, the α-hydrazino acetyl and alkyl hydrazine functionalities are much more nucleophilic than are the simple amines and alkoxy amine (e.g., 30- and 100-fold greater k1 value than ethyl amine, respectively), and are therefore the optimal nucleophiles for reacting with a thioester to form a stable linkage.

Figure 2:
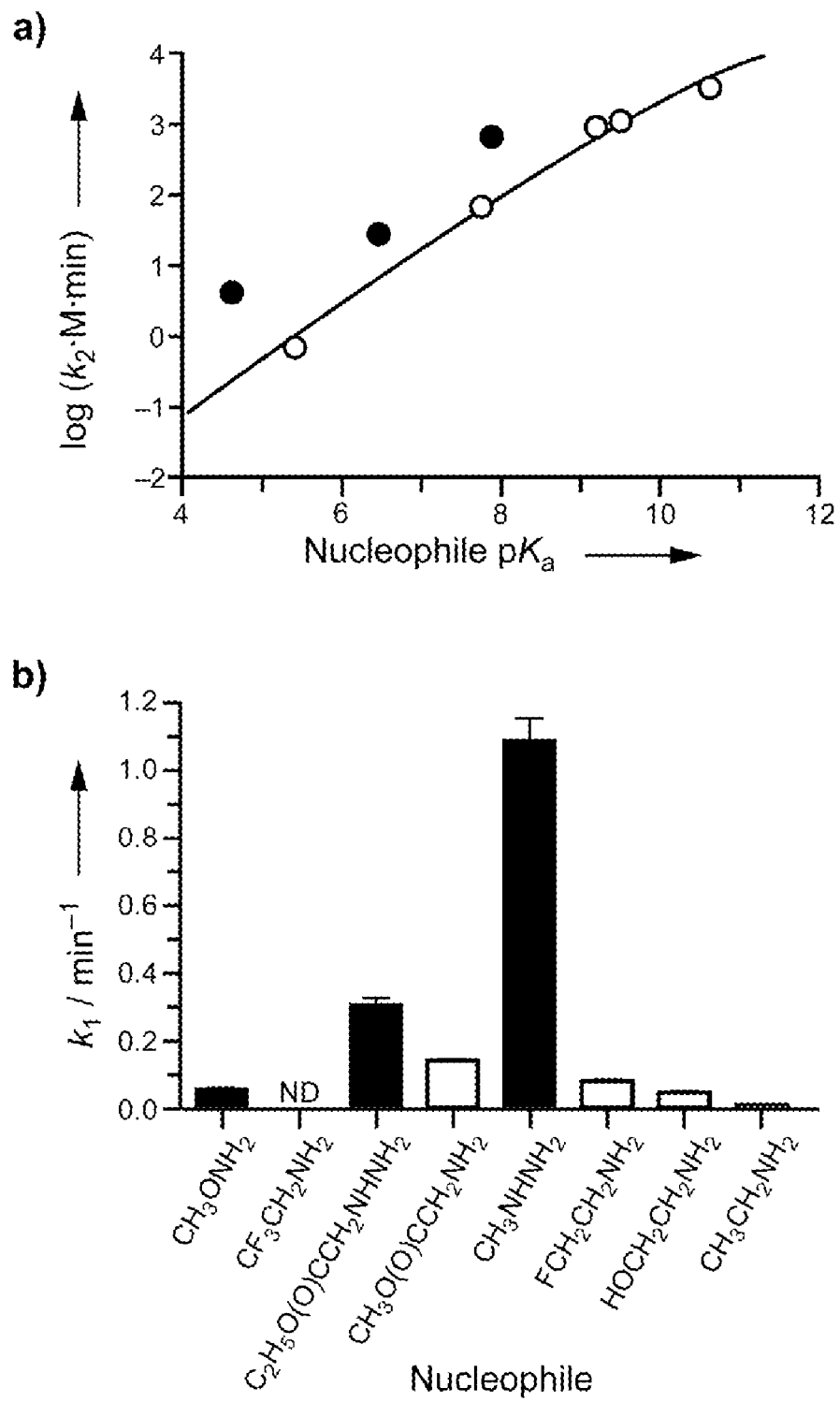
FIG. 2 provides rate constants for the attack of nitrogen nucleophiles on a thioester (Scheme 1). (a) Brønsted plot for the reaction of simple amines (open circles) and α-effect nucleophiles (filled circles) with AcGlySC$_6$H$_4$-p-NO$_2$ at 25° C. Relevant pKa values are listed in Table 1. Data were fitted to eq 1 with A=0.21, B=4.0×10-5, β=0.42, and β'=0.81. (b) Values of the first-order rate constant (k1) at pH 7.0 and 25° C. ND: not determined.

Jencks [29,33], Bruice [30], Castro [28,34] and others have reported in detail on the mechanism and kinetics of the nucleophilic attack on esters and, to a lesser extent, thioesters. This previous work was not, however, performed with the intent of making a stable linkage with a bifunctional reagent. For example, hydroxylamine was identified in 1950 as an exceptional nucleophile for a thioester [35]. Indeed, this attribute of hydroxylamine has led to its use in revealing transient thioesters formed during intein-mediated protein splicing [36]. The cleavage of thioesters by hydroxylamine relies, however, on the formation of an O-acylated hydroxylamine intermediate [37] that is inaccessible during the attack of an alkoxy amine on a thioester. Accordingly, an alkoxy amine is not an especially potent nucleophile for a thioester (FIG. 2).

Example 2

Synthesis of Bifunctional Azides

After identification of two optimal nucleophiles, we proceeded to synthesize two bifunctional reagents bearing those nucleophiles on one end and an azido group on the other. Azides 1 and 2 are both amides of 1-azido-2-aminoethane. Azide 1 has an α-hydrazino acetamido group, which is a more stable analog of the α-hydrazino acetyl group of $C_2H_5O(O)CCH_2NHNH_2$ (Table 1; FIG. 2); azide 2 has a γ-hydrazino acetamido group and is effectively an alkyl hydrazine.

Scheme 2. Synthetic route to azide 1.

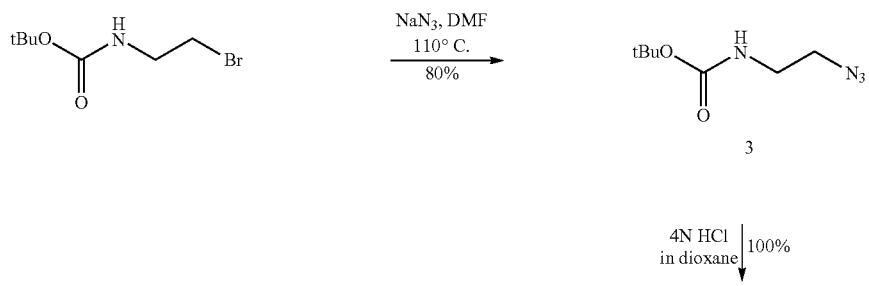

-continued

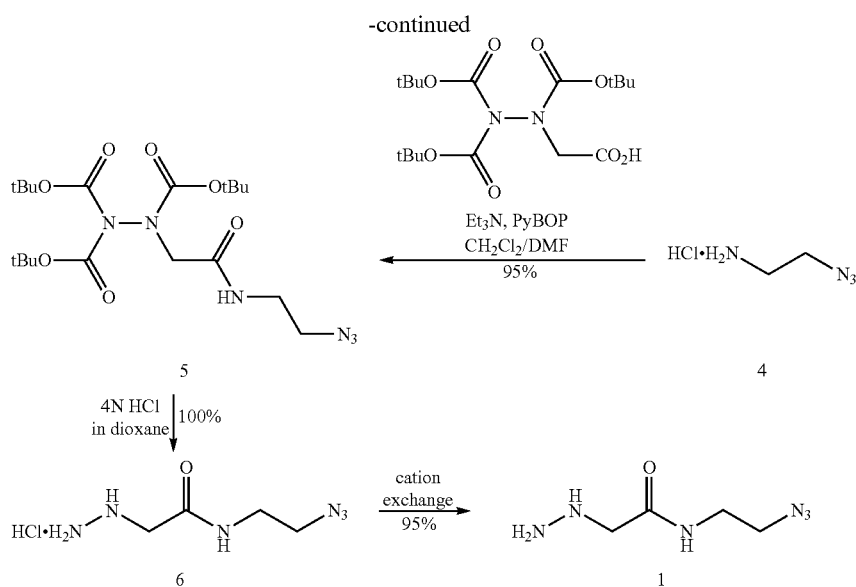

Azide 1 was synthesized by the route in Scheme 2. Briefly, Boc-protected 1-azido-2-aminoethane was synthesized from Boc-protected 1-bromo-2-aminoethane. After Boc-deprotection, the amine was coupled to tri-Boc-protected α-hydrazino acetic acid. The Boc groups were removed, and azide 1 was isolated as a free base after cation-exchange chromatography with an overall yield of 72%.

Scheme 3. Synthetic route to azide 2.

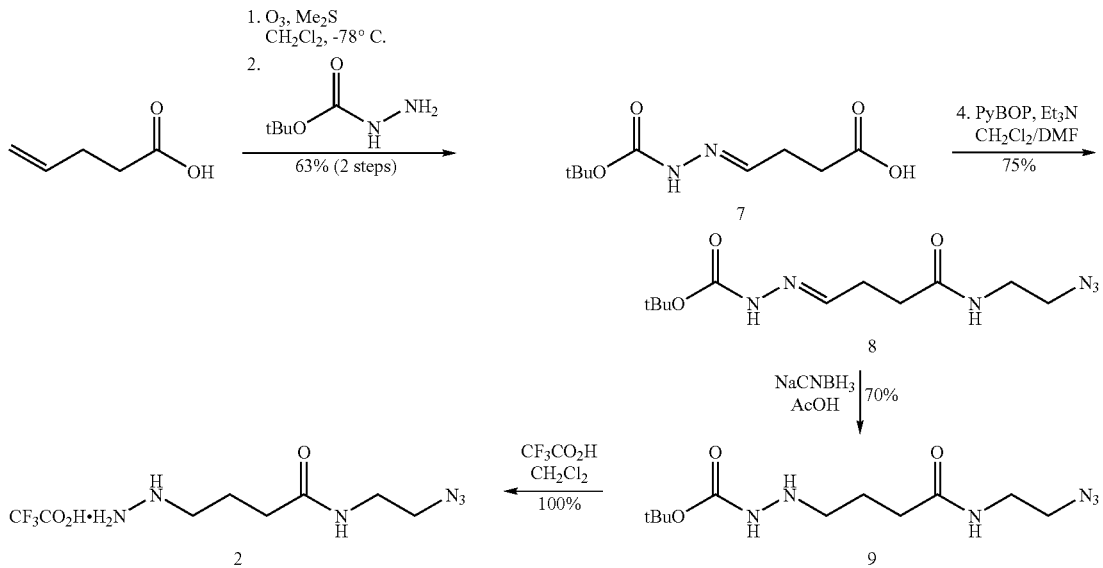

Azide 2 was synthesized by the route in Scheme 3. Briefly, 4-pentenoic acid was subjected to ozonolysis, and the resulting aldehyde was reacted in-situ with Boc-protected hydrazine. The azido group was installed by coupling 1-azido-2-aminoethane (4) to the carboxylic acid. The hydrazone was then reduced selectively with NaCNBH$_3$. The Boc group was removed to produce azide 2 as its trifluoroacetic acid (TFA) salt with an overall yield of 26% (which includes the 80% yield for the synthesis of azide 3). Attempts to produce the free hydrazine base by cation-exchange chromatography resulted in decomposition of the molecule by an (as yet) unknown mechanism. Likewise, the TFA salt was unstable even upon storage under vacuum, and hence was used immediately after its synthesis.

Hetero bifunctional reagent 100 was prepared as illustrated in Scheme 5. In this reagent the hydrazine group and the azido group are separated by an ether linker, specifically a triethylene glycol spacer. The illustrated method can also be employed to prepare reagents having a polymeric PEG or Pegylated linker.

Scheme 5

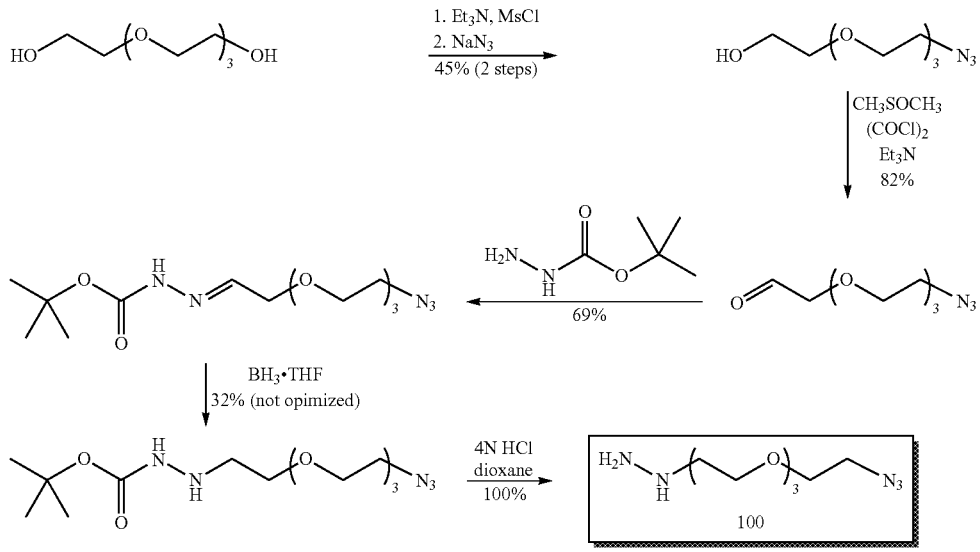

Example 3

Kinetics of Thioester Cleavage

Kinetic studies were performed by reacting azides 1 and 2 with a model chromogenic thioester (Scheme 1).

Scheme 1. Cleavage reaction of a model chromogenic thioester.

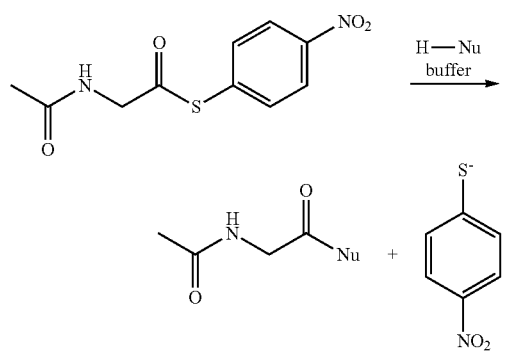

The rate constants ($k_2$ and $k_1$) for azide 1 were found to be indistinguishable from those of the α-hydrazino acetyl group. The rate constants for azide 2 were, surprisingly, much lower than those of methylhydrazine. This result is contrary to our finding that methyl hydrazine is a somewhat better nucleophile than the α-hydrazino acetyl functional group (FIG. 2). The intrinsic instability of azide 2 is likely to be responsible for this apparent decrease in reactivity.

Example 4

Production of an Azido-Protein

Figure 3:
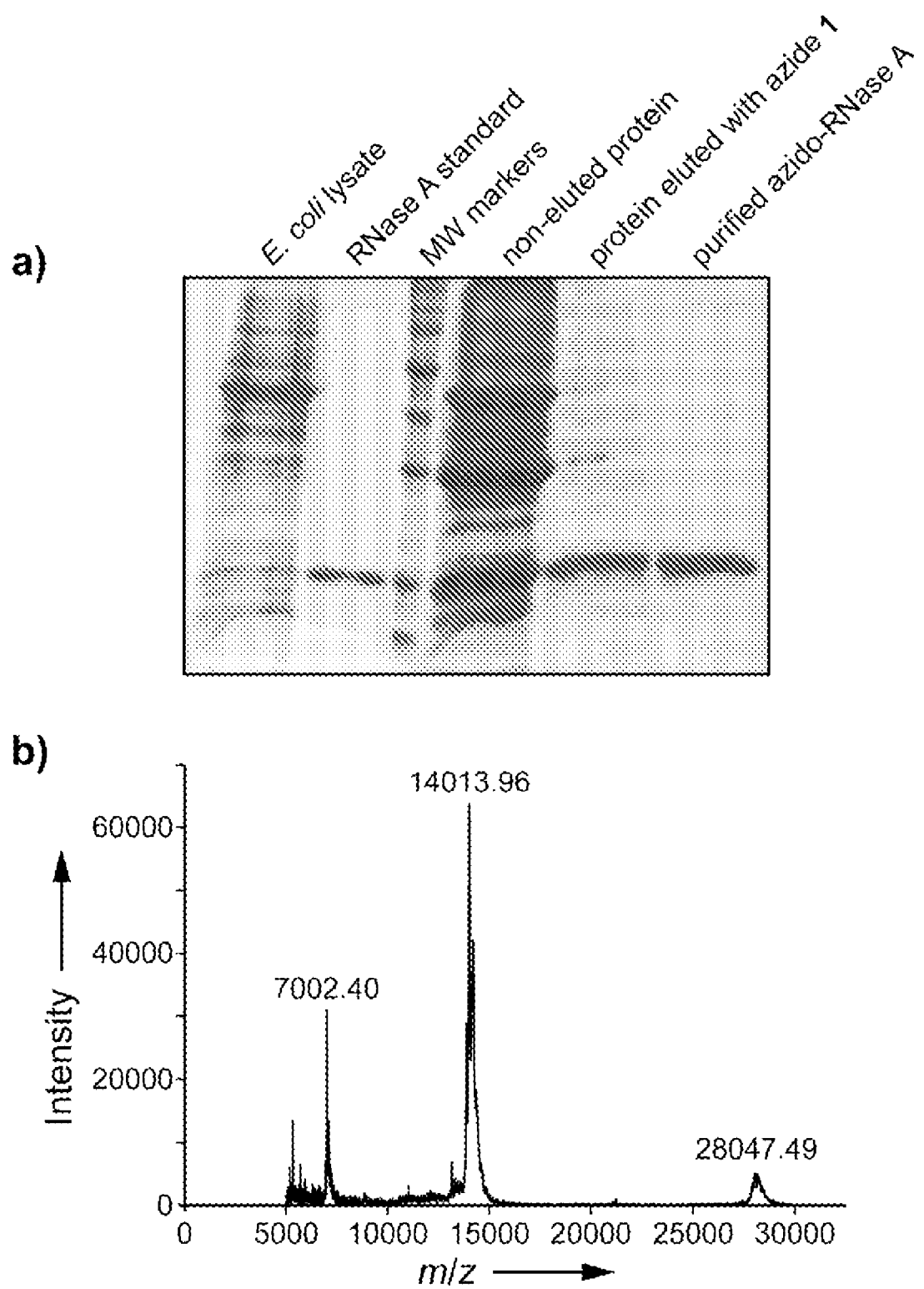
FIG. 3 illustrates (a) SDS-PAGE analysis of the preparation of azido-RNase A and (b) MALDI-TOF mass spectrum of azido-RNase A (expected for Met(-1)RNase A-Gly-NHNHCH$_2$C(O)NHCH$_2$CH$_2$N$_3$ [C$_{586}$H$_{929}$N$_{179}$O$_{195}$S$_{13}$]= 14011).

Next, we sought to use our bifunctional reagents to install an azido group at the C terminus of a model protein. As our protein, we chose bovine pancreatic ribonuclease (RNase A), which has been the object of much seminal work in protein chemistry [38] and has been manipulated previously with expressed protein ligation [39-41]. RNase A has valine as its C-terminal residue. A valine residue at the C terminus of a target protein is known to have a debilitating effect on the cleavage efficiency of protein-intein thioesters [12,42]. To avert this problem, we inserted a glycine residue between the C terminus of RNase A and the intein. The resulting Met(−1) RNase A-Gly-mxe intein-chitin-binding domain fusion protein (MW ~36 kDa) was produced in E. coli, and the cell lysate was loaded onto chitin resin. Azides 1 and 2 were used to induce the on-resin cleavage of the fusion protein. As expected from the kinetic studies, azide 1 was found to be much more effective than azide 2 in cleaving the Met(−1) RNase A-Gly-mxe intein thioester. Its shorter and higher yielding synthesis, superior stability, and higher cleavage efficiency makes azide 1 the optimal bifunctional reagent for the semisynthesis of proteins labeled with the azido group. The purity of the azido-RNase A (even upon elution from the chitin column) was apparent from SDS-PAGE analysis (FIG. 3A); the integrity of the azido-RNase A was verified by using MALDI-TOF mass spectrometry (FIG. 3B). This procedure produced an overall yield of ~1 mg of purified azido-RNase A per liter of E. coli culture.

Incubating a protein with a potent nucleophile, such as the α-hydrazino acetamido group of azide 1, could compromise the structure of the protein. For example, the target protein in this study has 142 amide bonds in its main chain and side chains that could be attacked by the α-hydrazino acetamido group, but only one thioester bond. In addition, the target protein has eleven amino groups that could serve as intramolecular nucleophiles for that thioester bond. Enzymatic catalysis provides an extremely sensitive measure of native protein structure [43]. This measure is especially useful for detecting the inadvertent modification of RNase A, as one of its eleven amino groups is both especially reactive and critical for enzymatic activity [38,44]. Purified azido-RNase A had $k_{cat}/K_M=(3.2\pm1.0)\times10^7$ $M^{-1}s^{-1}$ for the cleavage of RNA. This value was in gratifying agreement with that of the wild-type enzyme, which had $k_{cat}/K_M=(5.2\pm0.4)\times10^7$ $M^{-1}s^{-1}$.[45]

The α-hydrazino acetamido group was found to be the optimal nitrogen nucleophile for producing azido-proteins.

Still, a 450 mM solution of azide 1 was needed to produce the desired hydrazide product. Using lower concentrations lead to hydrolyzed protein (that is, the protein with a C-terminal carboxyl group) being a dominant product. In contrast, a 50 mM solution of thiol typically suffices for transthioesterification during expressed protein ligation [11]. The resulting thioester must then, however, react with a peptide (present in vast excess) that contains an N-terminal cysteine residue [12. 13]. The ability to obtain an azido-protein in a single step by on-resin cleavage and the absence of the residual sulfhydryl group installed during expressed protein ligation are noteworthy advantages of the inventive strategy (FIG. 1). These attributes are of particular importance for high-throughput procedures, such as the fabrication of protein microarrays [46].

Example 5

Huisgen 1,3-dipolar Cycloaddition to an Azido-Protein

Figure 4:
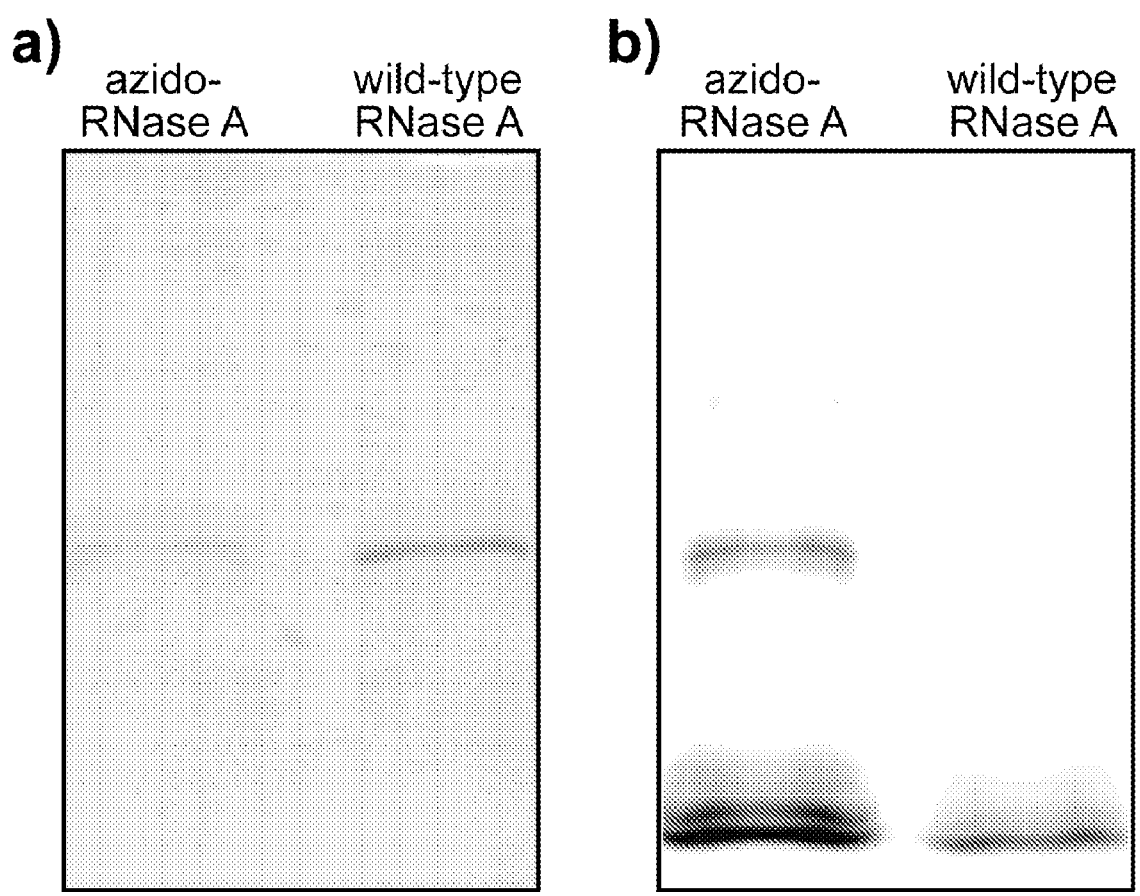
FIG. 4 illustrates SDS-PAGE analysis of the reaction of azido-RNase A and wild-type RNase A with alkynyl fluorescein 10.
Figure 5:
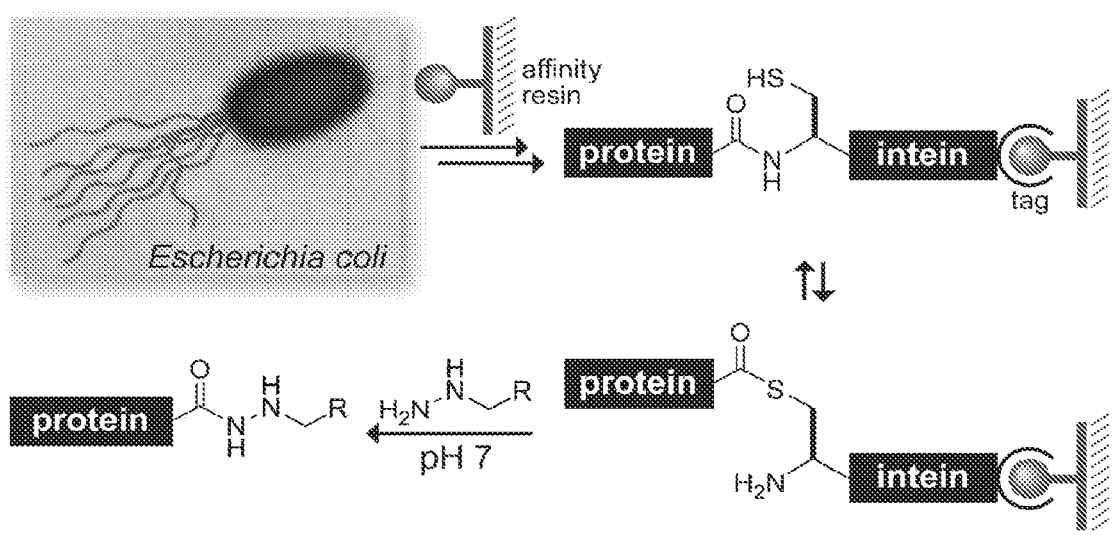
FIG. 5 is an illustration of intein-mediated generation of a protein thioester followed by reaction with a hydrazine of this invention to functionalize the protein.

For our strategy to be useful, the azido group in azido-RNase A must be available for further reaction. We used a chemoselective reaction, Cu(I)-catalyzed Huisgen 1,3-dipolar azide-alkyne cycloaddition [18,47,48], to probe for the availability of the azide functionality. To effect this "functional group test", alkynyl fluorescein 10 was synthesized by the route in Scheme 4. Azido-RNase A was reacted with 10 in the presence of the Cu(I) catalyst and its polytriazole ligand [48]. The resulting protein had a molecular mass of m/z=14449, which agreed well with that expected for the conjugate ($[C_{610}H_{936}N_{180}O_{201}S_{13}]$=14424). The protein was also subjected to SDS-PAGE and visualized by staining with Coomassie blue and fluorescence imaging. The azido-RNase A was found to be fluorescent as a result of the cycloaddition, whereas wild-type RNase A treated in the same manner was not fluorescent (FIG. 4). Neither the mass spectrum nor the SDS-PAGE gel showed evidence of cleavage products, as have been observed in an azido-protein exposed to reducing agents [49]. Thus, an azido group was not only installed into a specific site on RNase A, but also was available for reaction. In on-going work, the Staudinger ligation [19] is being used for the site-specific immobilization of proteins produced by the novel route shown in FIG. 1.

Scheme 4. Synthetic route to alkynyl fluorescein 10.

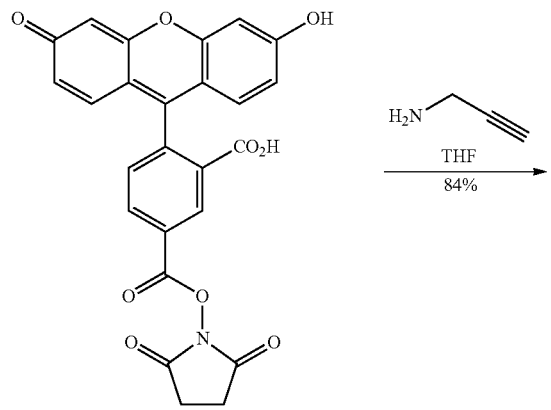

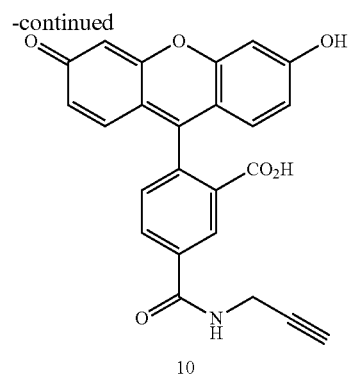

10

The chromogenic thioester $AcGlySC_6H_4$-p-$NO_2$ was a generous gift from Dr. B. L. Nilsson,[40] and was purified by re-crystallization from methylene chloride and stored in a tightly sealed vial in a desiccator to prevent hydrolysis due to moisture present in air. Fluorescein-NHS ester was a generous gift from L. D. Lavis. All other chemicals were commercial reagent grade or better, and were used as received except for benzyl azide, which was purified by flash chromatography before use. Anhydrous THF, DMF, and $CH_2Cl_2$ were obtained from a CYCLE-TAINER® solvent delivery system (J. T. Baker, Phillipsburg, N.J.). Other anhydrous solvents were obtained in septum-sealed bottles. Synthetic reactions were monitored by thin-layer chromatography (TLC) with visualization by UV-light or staining with vanillin, ninhydrin, or $I_2$. In all reactions involving anhydrous solvents, glassware was flame-dried. Flash chromatography was performed with columns of silica gel 60, 230-400 mesh (Silicycle, Quebec City, Quebec, Canada).

Example 6

Experimental Detail for Examples 1-5

Instrumentation: A Cary Model 3 UV/VIS spectrophotometer (Varian, Palo Alto, Calif.) was used to perform kinetic assays and measure ultraviolet absorbance. NMR spectra were acquired with a Bruker AC+ 300 spectrometer ($^1$H: 300 MHz, $^{13}$C: 75 MHz) at the Magnetic Resonance Facility in the Department of Chemistry or (as indicated) Bruker DMX-400 Avance spectrometer (1H: 400 MHz, $^{13}$C: 100 MHz) at the National Magnetic Resonance Facility at Madison (NM-RFAM). Carbon-13 spectra were proton-decoupled. Mass spectra on small organic molecules were obtained with electrospray ionization (ESI) techniques. Mass spectra of proteins were obtained with matrix-assisted laser desorption ionization-time-of-flight (MALDI-TOF) mass spectrometry using a Voyager-DE-PRO Biospectrometry workstation (Applied Biosystems, Foster City, Calif.) and a 3,5-dimethoxy-4-hydroxycinnamic acid (sinapinic acid) matrix (Aldrich). Fluorescence measurements were made with a QuantaMaster 1 photon counting fluorometer equipped with sample stirring (Photon Technology International, South Brunswick, N.J.). A Typhoon 9410 variable mode fluorimager (Amersham Biosciences) was used to visualize fluorescein-labeled protein after SDS-PAGE.

Kinetics of thioester cleavage: $AcGlySC_6H_4$-p-$NO_2$ was dissolved in anhydrous acetonitrile to a concentration of 0.45 mM and used immediately. Amine solutions (except $CF_3CH_2NH_2$.HCl) were prepared by dissolving the amine hydrochloride salts in 0.10 M sodium phosphate buffer at pH 7.0 to a concentration of 0.15 M. Reaction mixtures were prepared in a 1,1-mL volume and equilibrated at 25° C. All reactions contained ≦0.3% v/v acetonitrile. The ionic strength of each reaction mixture was I=0.22-0.25. All reactions were carried out with a large excess of amine and followed pseudo-first-order kinetics. In a cuvette containing 0.10 M sodium phosphate buffer at pH 7.0 (967 µL), amine solution (0.15 M, 100 µL) was added and the absorbance at 410 nm was adjusted to zero. The thioester (33 µL of a 0.45 mM solution in acetonitrile) was then added to the cuvette, and the absorbance at 410 nm was monitored with time ($\epsilon$=11,230 $M^{-1}cm^{-1}$ for p-nitrothiophenolate anion [40]). The $pK_a$ of $HSC_6H_4$-p-$NO_2$ is 4.77 in 40% v/v ethanol in water [50]. This value is likely to be lower in an aqueous buffer, such that the ionization of the p-nitrothiophenol product is virtually complete in all our assays. The final concentration of the thioester in the reaction was 13.64 µM and the final concentration of the amines (except $CF_3CH_2NH_2$.HCl) was 13.64 mM. Each reaction was performed in triplicate. The reactions were allowed to go to completion, and the $t_{1/2}$ was determined from the kinetic trace. The $t_{1/2}$ was corrected by subtracting the $t_{1/2}$ for hydrolysis from the observed value. Pseudo-first-order rate constants were calculated by using the equation $k_1=0.693/t_{1/2}$. Second-order rate constants were obtained by dividing each observed first-order rate constant by the concentration of free amine. Logarithmic values of second-order rate constants were plotted against the $pK_a$ values of the conjugate acids of the respective amines to yield a Brønsted plot.

Kinetics of Thioester Cleavage by $CF_3CH_2NH_2$: The procedure for the kinetics of thioester cleavage (vide supra) was found to be problematic for $CF_3CH_2NH_2$ because this amine is a poor nucleophile at pH 7.0. Indeed, the rate of hydrolysis was found to be greater than the rate of aminolysis by $CF_3CH_2NH_2$ under standard reaction conditions. Using a higher concentration of the hydrochloride salt (40.92 mM) resulted in the changing of the final reaction pH to 5.8. Using a higher buffer concentration was not ideal, as that would increase the ionic strength to a much value much larger than that in other reaction mixtures. To overcome these problems, the reaction with $CF_3CH_2NH_2$ was carried out using 40.92 mM $CF_3CH_2NH_2$.HCl and allowing the pH of the reaction mixture to decrease to 5.8. The observed $t_{1/2}$ was corrected by subtracting the $t_{1/2}$ for hydrolysis at pH 5.8. The second-order rate constant was calculated by accounting for the concentration of free amine at pH 5.8, and the resulting value was used in the Brønsted plot. The first-order rate constant thus obtained was not compared to those for the other nucleophiles.

Synthesis of $BocNHCH_2CH_2N_3$ (3): $BocNHCH_2CH_2Br$ (10.00 g, 44.62 mmol) was dissolved in DMF (200 mL). $NaN_3$ (14.48 g, 223.1 mmol) was added, and the mixture was stirred at 110° C. for 12 h. The solvent was removed under reduced pressure, and the residue was dissolved in water (200 mL). The resulting aqueous solution was extracted with ethyl acetate (2×200 mL). The organic layers were combined and dried over anhydrous $MgSO_4$(s). After filtering, the organic layer was concentrated under reduced pressure and the residue was dissolved in methylene chloride (10-20 mL) and purified by flash chromatography (silica gel, methylene chloride). $BocNHCH_2CH_2N_3$ (6.60 g, 80%) was isolated as a colorless oil. HRMS (ESI) $[M+Na]^+$ calcd for $C_7H_{14}N_4O_2Na$, 209.1014; found, 209.1010; $^1H$ NMR (400 MHz, $CDCl_3$) δ 4.88 (bs, 1H), 3.42 (t, J=5.3 Hz, 2H), 3.34-3.26 (m, 2H), 1.45 (s, 9H); $^{13}C$ NMR (100 MHz, $CDCl_3$) δ 155.8, 79.8, 51.4, 40.2, 28.5.

Synthesis of $(Boc)_2NN(Boc)CH_2CONHCH_2CH_2N_3$ (5): $HCl.H_2NCH_2CH_2N_3$ (4) was synthesized by dissolving azide 3 (2.11 g, 11.33 mmol) in 4 N HCl in dioxane (100 mL) and stirring at room temperature for 1 h. The solvent was removed under reduced pressure to give a dirty white powder. $(Boc)_2NN(Boc)CH_2CO_2H$ (4.42 g, 11.33 mmol) was then added, and the mixture was dissolved in methylene chloride/DMF (70:45 mL). The mixture was cooled to 0° C., and PyBOP (5.9 g, 11.33 mmol) and $Et_3N$ (3.2 mL, 22.66 mmol) were added. The reaction mixture was allowed to warm to room temperature and stirred under Ar(g) for 21 h. The solvent was removed under reduced pressure, and the residue was purified by flash chromatography (silica gel, 50% v/v ethyl acetate in hexanes) to give $(Boc)_2NN(Boc)CH_2CONHCH_2CH_2N_3$ as a colorless viscous oil (4.9 g, 95%). HRMS (ESI) $[M+Na]^+$ calcd for $C_{19}H_{34}N_6O_7Na$, 481.2387; found, 481.2389; $^1H$ NMR (400 MHz, $CDCl_3$, 2 rotamers) δ 8.51 and 8.27 (bs, 1H), 4.06 and 3.99 (s, 2H), 3.49-3.40 (m, 4H), 1.56-1.44 (m, 27H); $^{13}C$ NMR (100 MHz, $CDCl_3$, 2 rotamers) δ 169.5, 169.2, 154.0, 153.5, 151.4, 151.2, 85.2, 85.1, 83.5, 82.8, 56.5, 54.8, 50.6, 38.9, 34.1, 29.9, 28.2, 28.1.

Synthesis of $H_2NNHCH_2CONHCH_2CH_2N_3$ (1): Azide 5 (4.66 g, 10.17 mmol) was dissolved in 4 N HCl in dioxane (200 mL), and the solution was stirred at room temperature for 5 h. Solvent was removed under reduced pressure, and the residue was dissolved in water (15 mL) and purified by cation-exchange chromatography (Dowex 50WX8-200 ion-exchange resin, 1 M $NH_4OH$) to give $H_2NNHCH_2CONHCH_2CH_2N_3$ as a yellow oil (1.52 g, 95%). HRMS (ESI) $[M+Na]^+$ calcd for $C_4H_{10}N_6ONa$, 181.0814; found, 181.0805; $^1H$ NMR (300 MHz, $d_6$-DMSO) δ 8.03 (app bs, 1H), 3.80-3.40 (bs, 3H), 3.40-3.34 (m, 2H), 3.32-3.24 (m, 2H), 3.16 (s, 2H); $^{13}C$ NMR (75 MHz, $d_6$-DMSO) δ 171.2, 57.1, 50.0, 37.8.

Synthesis of BocNHN=$CHCH_2CH_2CO_2H$ (7): 4-Pentenoic acid (10.00 g, 99.88 mmol) was dissolved in methylene chloride (150 mL), and the mixture was cooled to -78° C. under $N_2$(g). Ozone was bubbled through the reaction mixture, and the course of the reaction was monitored by TLC. After TLC showed disappearance of the starting material (ca. 2.5 h), methyl sulfide (15.0 mL, 205.23 mmol) was added and the reaction mixture was allowed to warm to room temperature. Subsequently, solvent was removed under reduced pressure, and the residue was dissolved in THF (200 mL). $BocNHNH_2$ (13.2 g, 99.88 mmol) was then added, and the reaction mixture was refluxed overnight under Ar(g). Solvent was removed under reduced pressure, and the residue was purified by flash chromatography (silica gel, 6% v/v methanol in methylene chloride) to give BocNHN=$CHCH_2CH_2CO_2H$ as a white solid (13.60 g, 63%). HRMS (ESI) $[M-H]^-$ calcd for $C_9H_{15}N_2O_4$, 215.1032; found, 215.1035; $^1H$ NMR (300 MHz, $d_6$-DMSO) δ 12.16 (s, 1H), 10.45 (s, 1H), 7.30 (app bs, 1H), 2.45-2.30 (m, 4H), 1.41 (s, 9H); $^{13}C$ NMR (100 MHz, $d_6$-DMSO) δ 173.5, 152.4, 145.6, 78.9, 30.4, 28.1, 27.2.

Synthesis of BocNHN=$CHCH_2CH_2CONHCH_2CH_2N_3$ (8): $HCl H_2NCH_2CH_2N_3$ (4) was synthesized as described earlier. Compound 7 (4 g, 18.5 mmol) and $HCl.H_2NCH_2CH_2N_3$ (2.27 g, 18.5 mmol) were dissolved in methylene chloride/DMF (180:70 mL). The mixture was cooled to 0° C., and PyBOP (9.63 g, 18.5 mmol) and $Et_3N$ (20 mL, 142.8 mmol) were then added. The reaction mixture was allowed to warm to room temperature and stirred for 21 h. Solvent was removed under reduced pressure, and the residue was purified by flash chromatography (silica gel, ethyl acetate). BocNHN=$CHCH_2CH_2CONHCH_2CH_2N_3$ was obtained as a white solid (3.94 g, 75%). HRMS (ESI) $[M+Na]^+$ calcd for $C_{11}H_{20}N_6O_3Na$, 307.1495; found, 307.1494; $^1H$ NMR (300 MHz, $d_6$-DMSO) δ 10.43 (bs, 1H), 8.13 (t, J=5.3 Hz, 1H), 7.28 (app bs, 1H), 3.33 (t, J=5.7 Hz, 2H), 3.28-3.19 (m, 2H), 2.4-2.3 (m, 2H), 2.29-2.22 (m, 2H), 1.41 (s, 9H); $^{13}$C NMR (100 MHz, $d_6$-DMSO) δ 171.6, 152.5, 146.1, 79.0, 50.0, 38.3, 32.1, 28.2, 27.8.

Synthesis of BocNHNHCH$_2$CH$_2$CH$_2$CONHCH$_2$CH$_2$N$_3$ (9): Compound 8 (1.12 g, 3.9 mmol) was dissolved in acetonitrile (27 mL), and acetic acid (3.7 mL). NaCNBH$_3$ (1.11 g, 16.75 mmol) was added to the resulting solution. The reaction mixture was stirred at room temperature for 3 h. Solvent was removed under low pressure, and the residue was dissolved in water (45 mL). The pH of the solution was increased to 13.0 by adding 10 N NaOH, and the aqueous solution was extracted with ether (3×45 mL) and then methylene chloride (50 mL). The organic layers were combined and dried over anhydrous MgSO$_4$(s). After filtering, the organic layer was concentrated under reduced pressure, and the residue was purified by flash chromatography (silica gel, 2% v/v methanol in methylene chloride) to give BocNHNHCH$_2$CH$_2$CH$_2$CONHCH$_2$CH$_2$N$_3$ as a colorless oil (0.78 g, 70%). HRMS (ESI) [M+Na]$^+$ calcd for C$_{11}$H$_{22}$N$_6$O$_3$Na, 309.1651; found, 309.1641; $^1$H NMR (300 MHz, $d_6$-DMSO, 2 rotamers) δ 8.15 (bs, 1H), 8.09-7.90 (m, 1H), 4.34 (bs, 1H), 3.32 (t, J=5.7 Hz, 2H), 3.26-3.18 (m, 2H), 2.66-2.53 (m, 2H), 2.22-2.07 (m, 2H), 1.64-1.48 (m, 2H), 1.46-1.22 (m, 9H); $^{13}$C NMR (100 MHz, $d_6$-DMSO, 2 rotamers) δ 172.5, 156.4, 78.2, 56.1, 54.9, 50.4, 50.0, 38.2, 33.0, 28.2, 23.5, 22.9.

Synthesis of CF$_3$CO$_2$H.H$_2$NNHCH$_2$CH$_2$CH$_2$CONHCH$_2$CH$_2$N$_3$(2): Compound 9 (197.8 mg, 0.69 mmol) was dissolved in methylene chloride (6.4 mL), and trifluoroacetic acid (6.4 mL) was added to the resulting solution. The reaction mixture was stirred at room temperature for 15 min. Solvent was removed under reduced pressure to afford CF$_3$CO$_2$H.H$_2$NNHCH$_2$CH$_2$CH$_2$CONHCH$_2$CH$_2$N$_3$ as a yellow oil (130 mg, 100%). HRMS (ESI) [M+H]$^+$ calcd for C$_6$H$_{15}$N$_6$O, 187.1307; found, 187.1299; $^1$H NMR (400 MHz, $d_6$-DMSO) δ 8.19 (t, J=4.8, 1H), 7.9-5.5 (bs, 3H), 3.34 (t, J=5.8, 2H), 3.28-3.20 (m, 2H), 2.89 (t, J=7.5 Hz, 2H), 2.21-2.11 (m, 2H), 1.85-1.68 (m, 2H); $^{13}$C NMR (100 MHz, $d_6$-DMSO) δ 171.9, 50.1, 50.0, 38.2, 32.2, 21.0.

Synthesis of alkynyl fluorescein 10: Fluorescein-NHS ester (100 mg, 0.21 mmol) was dissolved in THF (10 mL) and propargylamine (23.27 mg, 0.42 mmol) was added. The reaction mixture was stirred at room temperature for 4 h. Solvent was removed under reduced pressure, and the residue was purified by flash chromatography (silica gel, 35% v/v hexanes in ethyl acetate containing 1% v/v AcOH) to give the desired product as a red solid (72.80 mg, 84%). HRMS (ESI) [M+Na]$^+$ calcd for C$_{24}$H$_{15}$NO$_6$Na, 436.0797; found, 436.0777; $^1$H NMR (400 MHz, $d_6$-DMSO) δ 10.20 (bs, 2H), 9.31 (t, J=5.1 Hz, 1H), 8.47 (s, 1H), 8.25 (dd, J=7.9, 1.4 Hz, 1H), 7.39 (d, 8.3 Hz, 1H), 6.68 (d, J=2.3 Hz, 2H), 6.59 (d, J=8.6 Hz, 2H), 6.54 (dd, J=8.7, 2.3 Hz, 2H), 4.11 (dd, J=5.3, 2.2 Hz, 2H), 3.17 (t, J=2.5 Hz, 1H); $^{13}$C NMR (100 MHz, $d_6$-DMSO) δ 168.1, 164.4, 159.7, 154.8, 151.9, 135.5, 134.7, 129.2, 126.7, 124.4, 123.5, 112.8, 109.1, 102.3, 83.8, 81.0, 73.1, 28.8.

Synthesis of polytriazole ligand: A polytriazole ligand for the Cu(I) catalyst was synthesized essentially as described.[48] Tripropargyl amine (0.56 g, 4.28 mmol) was dissolved in acetonitrile (5.7 mL), and benzyl azide (2 g, 15.02 mmol) and 2,6-lutidine (0.46 g, 4.28 mmol) were added to the resulting solution. The reaction mixture was cooled to 0° C., and Cu(CH$_3$CN)$_4$ PF$_6$ (81.25 mg, 0.22 mmol) was added. The reaction mixture was allowed to warm to room temperature and stirred under Ar(g) for 2½ days. The reaction mixture was filtered, and the white precipitate obtained was dried under high vacuum to yield the polytriazole ligand (0.34 g, 15%). HRMS (ESI) [M+Na]$^+$ calcd for C$_{30}$H$_{30}$N$_{10}$Na, 553.2553; found, 553.2570; $^1$H NMR (400 MHz, CDCl$_3$) δ 7.66 (s, 3H), 7.40-7.20 (m, 15H), 5.50 (s, 6H), 3.70 (s, 6H); $^{13}$C NMR (100 MHz, CDCl$_3$) δ 134.8, 129.2, 128.8, 128.1, 123.9, 54.2, 47.2.

Production of RNase A-intein-chitin-binding domain fusion protein. A plasmid that directs the expression of an RNase A-mxe intein-chitin-binding domain fusion protein was a generous gift from U. Arnold. A glycine codon was introduced between the RNase A and the mxe intein genes using the QuickChange site-directed mutagenesis kit from Stratagene (LaJolla, Calif.). The resulting plasmid, pJK01, was transformed into E. coli BL21 (DE3) cells, and the production of Met(−1)RNase A-Gly-intein-chitin binding domain fusion protein was induced as described previously [41].

Production of azido-ribonuclease A: Cells were resuspended in 20 mM 3-(N-morpholino)propane sulfonic acid (MOPS)-NaOH buffer at pH 6.8 containing NaCl (0.50 M), ethylenediaminetetraacetic acid (EDTA; 0.10 mM), and Triton X-100 (0.1% v/v). Cells were lysed with a French pressure cell, and the cell lysate was subjected to centrifugation at 15,000 g for 30 min. The supernatant was diluted to a final volume of 25 mL (per g of cells) and applied (flow rate: 0.75 mL/min) to a chitin column that had been equilibrated with the same buffer. The loaded resin was washed with two column-volumes of buffer and then with four column-volumes of 0.5 M MOPS-NaOH buffer at pH 7.0 containing NaCl (0.50 M) and EDTA (0.10 mM). Azide 1 was dissolved in the latter buffer to a concentration of 450 mM, and three column-volumes of this solution were loaded onto the resin, out of which, two column-volumes were allowed to flow through and one column-volume was allowed to sit on top of the resin. This incubation was carried out for three days at room temperature to enable the reaction to proceed to completion. The hydrazide product was eluted with three column-volumes of an aqueous solution of NaCl (2 M). Azido-RNase A was precipitated out of the eluate by adding an aqueous solution of sodium deoxycholate (NaDOC; to 0.72 mM) and trichloroacetic acid (TCA; to 260 mM). This precipitate was washed with acetone and dissolved in an aqueous solution of guanidine-HCl (4 M).

The solution of protein was added with gentle stirring in 20-μL aliquots into a refolding solution (50 mL) consisting of 100 mM Tris-HCl buffer at pH 8.0 containing NaCl (100 mM), reduced glutathione (1 mM), and oxidized glutathione (0.2 mM). The final concentration of guanidine-HCl was 0.05 M. The refolding solution was incubated at room temperature for 24 h.

The refolding solution was dialyzed for 12 h against 50 mM sodium acetate buffer at pH 5.0. The azido-protein was purified by cation-exchange chromatography as described previously [51].

Ribonucleolytic activity: Values of $k_{cat}/K_M$ for the enzymatic cleavage of a fluorogenic substrate, 6-carboxyfluorescein-dArU(dA)$_2$-6-carboxytetramethyl rhodamine, were determined as described previously [52].

Huisgen 1,3-dipolar cycloaddition: To a solution of azido-RNase A (9.6 μM) in 0.10 M potassium phosphate buffer at pH 8.0 (41.9 μL) were added alkynyl fluorescein 10 (1.1 μL, 2.23 mM suspension in 20% v/v ethanol in water), tris(2-carboxyethyl) phosphine hydrochloride (1.0 μL, 50 mM), CuSO$_4$.5H$_2$O (1.0 μL, 50 mM), and polytriazole ligand (5.0 μL, 20 mM suspension in 80% v/v t-butanol in water). The reaction mixture was agitated gently, and incubated at room temperature for 1 h and then at 4° C. for 16 h. The same procedure was followed for the control reaction with unmodified wild-type RNase A (Sigma Chemical, St. Louis, Mo.). Protein precipitation was observed in both reaction mixtures, as is common (but not well appreciated) during Cu(I)-catalyzed Huisgen 1,3-dipolar azide-alkyne cycloaddition to a protein,[47] obviating the calculation of a yield for this reaction. The reaction mixtures were subjected to centrifugation at 5900 g for 4 min, and the supernatant was discarded. The pellet was resuspended in 2× denaturing buffer (20 µL) and subjected to SDS-PAGE. The resulting gel was visualized with a fluorescence imager and was then stained with Coomassie blue.

Example 7

Site-Specific Enzyme Immobilization Using Staudinger Ligation

This example describes a general method for site-specific protein immobilization using the Staudinger ligation. The method is useful for the preparation of protein microarrays and provides a facile, bio-orthogonal and bio-compatible protein immobilization chemistry for generating uniformly oriented protein microarrays.

Bovine pancreatic ribonuclease (RNase A; EC 3.1.27.5) appended with a C-terminal azido functional group was immobilized on phosphinothioester-displaying self assembled monolayers (SAMs) of alkane thiols on gold surfaces. The immobilization proceeded selectively via the azide functionality on the enzyme. The immobilized enzyme retained enzymatic activity and bound its natural binding partner, the ribonuclease inhibitor protein (RI).

The non-proteinogenic azido group is bio-orthogonal because it is chemically inert to the functional groups found in nature. The azido group has been used for site-specific protein and peptide immobilization by the Huisgen's 1,3-dipolar azide-alkyne cycloaddition reaction [63, 64, 65] and the Staudinger ligation [65, 5, 13b]. A bifunctional reagent bearing an azido group and α-hydrazino acetamido group was used (as described above) to cleave a transient thioester generated on the C terminus of the target protein fused to an intein, thereby labeling the protein with an azido group. This method was used to install the azido group into ribonuclease A (RNase A) to generate azido-RNase A.

Figure 6:
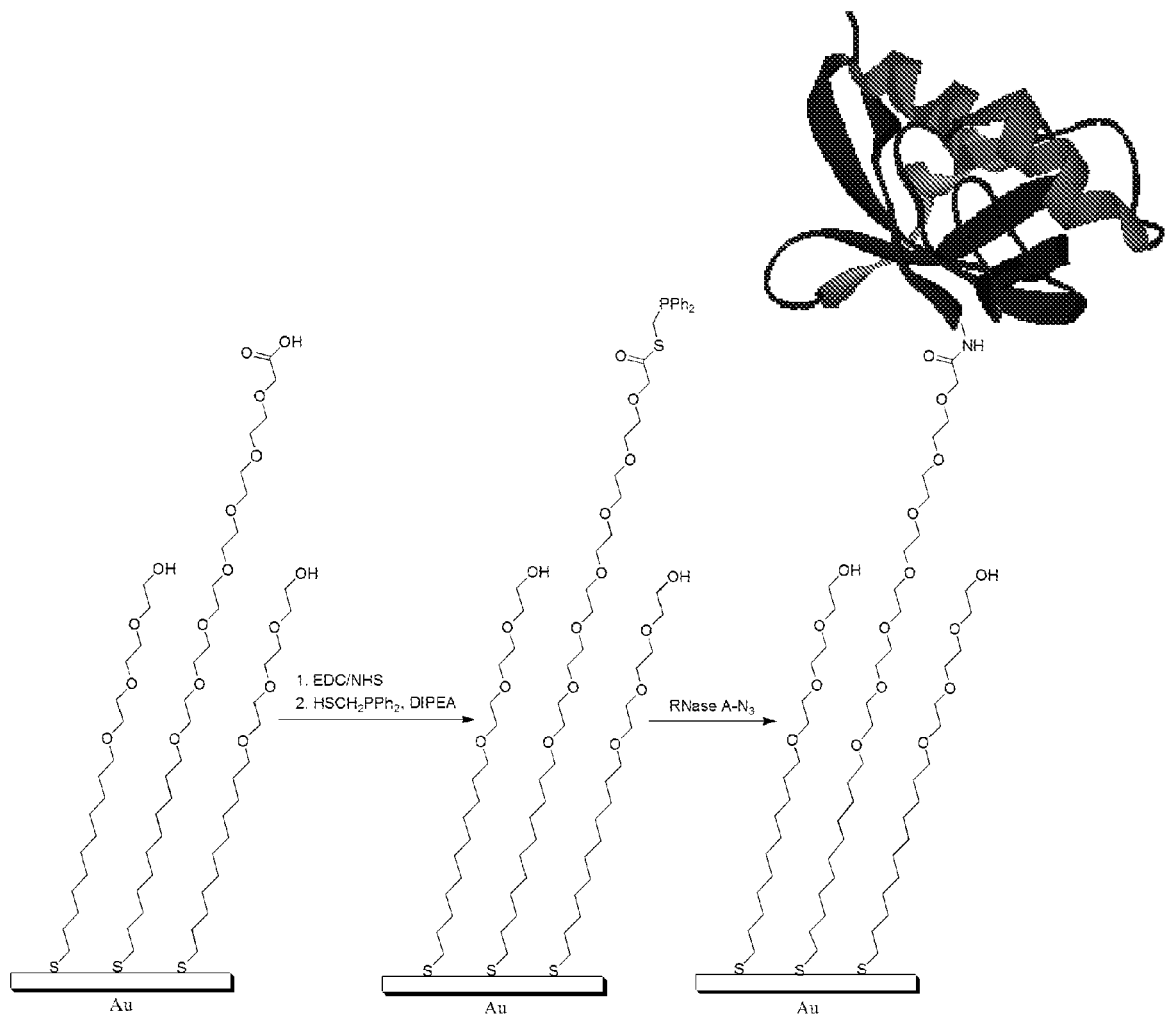
FIG. 6 is an illustration of site-specific enzyme immobilization by Staudinger ligation as described in Example 7.

This example describes a facile method for the site-specific immobilization of azido-RNaseA. RNase A was chosen as a model system for developing the immobilization chemistry. RNase A is renowned for its high stability and its interaction with ribonuclease inhibitor (RI) is one of the strongest known biological interactions [38]. The current method involves reacting azido proteins with phosphinothioester functional groups displayed on self assembled monolayers (SAMs) of alkane thiols on a gold surface (FIG. 6). The reaction of an azido group with a phosphinothioester is known as the Staudinger ligation [19b, 67] and is based on the Staudinger reaction [68] wherein a phosphine reduces an azide to form a stable amide bond. The version of the Staudinger ligation employed herein is traceless as it does not leave any residual atoms in the final amide product [69]. The reaction proceeds in high yields at room temperature, in aqueous solvents. The current strategy resulted in the immobilization of azido-RNase A exclusively via the azido group, and the immobilized enzyme was active and bound RI. This example demonstrates the proficiency of Staudinger ligation as a tool for site-specific protein immobilization and augurs well for the application of this reaction for the generation of protein microarrays.

Experimental Procedures

Materials. Reagents were from Sigma-Aldrich (St. Louis, Mo.). Anhydrous DMF and $CH_2Cl_2$ were withdrawn from a CYCLE-TAINER® solvent delivery system (Baker). Synthetic reactions were monitored by thin-layer chromatography with visualization by UV-light or staining with phosphomolybdic acid. For all reactions involving anhydrous solvents, glassware was flame-dried. Flash chromatography was performed with columns of silica gel 60, 230-400 mesh (Silicycle). A fluorogenic ribonuclease substrate, 6-carboxyfluorescein-dArU (dA)2-6-carboxytetramethyl-rhodamine, was from Integrated DNA Technologies (Coralville, Iowa). Two-hand AtmosBags™ were bought from Sigma-Aldrich (St. Louis, Mo.). Anti-RNase A rabbit primary antibody was from Biodesign International (Kennebunk, Me.). Alexa Fluor® 488-conjugated anti-rabbit secondary antibody was from Molecular Probes (Eugene, Oreg.). Anti-RI chicken primary antibody was from Genetel (Madison, Wis.). Fluorescein-conjugated anti-chicken secondary antibody was from Abcam (Cambridge, Mass.). Alkane thiols HS—$(CH_2)_{11}$—(O—$CH_2$—$CH_2)_6$—O—$CH_2$—COOH and HS—$(CH_2)_{11}$—(O—$CH_2$—$CH_2)_3$—OH were purchased from Prochimia (Gdansk, Poland). Wild-type RNase A was from Sigma Chemicals (St. Louis, Mo.).

Instrumentation. NMR spectra were acquired with a Bruker DMX-400 Avance spectrometer (1H: 400 MHz, 13C: 100 MHz) at the NMR Facility at Madison (NMRFAM). Mass spectra on small organic molecules were obtained with electrospray ionization (ESI) techniques. Fluorescence measurements for assaying RNase A activity were made with a QuantaMaster 1 photon counting fluorometer equipped with sample stirring (Photon Technology International, South Brunswick, N.J.). Immobilized RNase A, and RI bound to the immobilized RNase A were visualized with a Genomic Solutions® GeneTac UC4×4 Fluorescence Scanner. A Rudolf AutoEL ellipsometer was used to determine the optical thickness of SAMs and proteins on the surface of a gold film on Si wafer.

Preparation of Gold Chips (Chang). Preparation of Phosphinothioester-displaying SAMs of Alkane Thiols on Gold Chips. Alkane thiol solutions were prepared by dissolving HS—$(CH_2)_{11}$—(O—$CH_2$—$CH_2)_6$—O—$CH_2$—COOH and HS—$(CH_2)_{11}$—(O—$CH_2$—$CH_2)_3$—OH in ethanol to a final concentration of 0.25 mM each. Gold chips were cleaned under a stream of Ar(g) and immersed in the alkane thiol solution for at least 18 h at r.t. After rinsing thoroughly with ethanol and drying under a stream of Ar(g), the chips were overlaid with an aqueous solution containing N-hydroxysuccinimide (50 mM) and 1-ethyl-3-(3-dimethylaminopropyl)-carbodiimide (200 mM) for 7 min to generate succinimidyl ester-displaying chips. Phosphinomethanethiol ($PPh_2CH_2SH$) was synthesized as described earlier [70] and was dissolved in anhydrous DMF to a concentration of 100 mM. N,N-diisopropylethylamine (DIPEA) was added to a concentration of 120 mM. The resulting solution (in a 25 mL flask), succinimidyl ester displaying chips (in a Petri dish containing a water-soaked filter paper to serve as a humid chamber) and azido-RNase A (10 µM in 5% DMF/water) were placed in a two-hand AtmosBag™ along with vials containing anhydrous DMF (20 mL/vial), water (20 mL/vial), and sodium phosphate buffer (25 mM) at pH 7.5 (20 mL/vial). The AtmosBag™ was sealed and connected to the house vacuum on one end and an Ar(g) supply on the other end. The air inside the bag was removed using the house vacuum and it was flushed two times with Ar(g) before finally filling it up with Ar(g). The phosphinomethanethiol-DIPEA solution was transferred into the small empty vial and succinimidyl ester displaying chips were incubated in it for 2 h. The phosphinothioester-displaying chips thus produced were rinsed with DMF (2×20 mL) and then with water (2×20 mL).

Immobilization of azido-RNase A by Staudinger ligation. Azido-RNase A (1 µl, 10 µM in 5% DMF/water) was incubated on phosphinothioester-displaying chips for different time periods at r.t. inside the AtmosBag™. The chips were subsequently rinsed with sodium phosphate buffer (25 mM) at pH 7.5 (20 mL) and removed from the AtmosBag™. They were then incubated in sodium phosphate buffer (25 mM) at pH 7.5 (1 mL) for 30 min to remove non-specifically bound protein.

Detection of Immobilized RNase A. A chip displaying immobilized RNase A was overlaid with anti-RNase A rabbit primary antibody (100 µg/mL in sodium phosphate buffer (25 mM) at pH 7.5) for 30 min at r.t. The chip was then rinsed with sodium phosphate buffer (25 mM) at pH 7.5 (2×20 mL) and incubated in the same buffer for 15 min. It was subsequently overlaid with Alexa Fluor® 488-conjugated anti-rabbit secondary antibody (2.0 µg/mL in sodium phosphate buffer (25 mM) at pH 7.5) for 30 min at r.t. Finally, the chip was rinsed with sodium phosphate buffer (25 mM) at pH 7.5 (2×20 mL) and incubated in the same buffer for 15 min and scanned with a Genomic Solutions® GeneTac UC4×4 Fluorescence Scanner using a gain of 50.

RNase A activity assay on immobilized RNase A. A phosphinothioester chip was overlaid with azido-RNase A (10 µM in 5% DMF/H2O) for 15 min in Ar(g) atmosphere in an AtmosBag™ to immobilize RNase A via Staudinger ligation. The chip was rinsed with sodium phosphate buffer (25 mM) at pH 7.5 (2×20 mL) and then introduced into a vial containing 2-(N-Morpholino)ethanesulfonic acid buffer (0.1 M) at pH 6.0 (22 mL, containing 0.1 M NaCl). A fluorogenic substrate of RNase A, 6-carboxyfluorescein-dArU(dA)2-6-carboxytetramethylrhodamine (10 µl of a 40 µM solution), was introduced into the vial. The vial was placed on a shaker and 2 mL aliquots were withdrawn at various time intervals and the fluorescence measured ($\lambda_{ex}$=493 nm, $\lambda_{em}$=515 nm). The fluorescence intensity was plotted against time. A phosphinothioester chip was overlaid with wt-RNase A (10 µM in 5% DMF/H2O) and rinsed with sodium phosphate buffer (25 mM) at pH 7.5 (2×20 mL) and a similar assay was performed. As a negative control, a similar assay was performed on a phosphinothioester chip which was not overlaid with RNase A. The percentage of the fluorescent substrate cleaved at various time intervals were subtracted from the corresponding values for the negative control to generate the graph in FIG. 8.

RI binding to immobilized RNase A. Azido-RNase A (1 µL, 10 µM in 5% DMF/water) was spotted on phosphinothioester-displaying SAMs on a gold chip for 15 minutes at r.t. in an AtmosBag™ filled with Ar(g). The chip was taken out of the bag and rinsed with sodium phosphate buffer (25 mM) at pH 7.5 (2×20 mL) and incubated in the same buffer for 30 min to remove non-specifically bound RNase A. RI (10 µM in sodium phosphate buffer (25 mM) at pH 7.5 containing 10 mM DTT) was overlaid on the chip for 10 min at 4° C. The chip was then rinsed with sodium phosphate buffer (25 mM) at pH 7.5 containing 10 mM DTT (2×20 mL) and incubated in the same buffer for 15 min.

Detection of RI bound to immobilized RNase A. (i) Immunoassay: After RI binding, the chip was overlaid with bovine serum albumin (2.0 mg/mL in sodium phosphate buffer (25 mM) at pH 7.5) for 15 min. The chip was rinsed with sodium phosphate buffer (25 mM) at pH 7.5 (2×20 mL) and subsequently incubated with chicken primary antibody to RI (12.5 µg/mL in sodium phosphate buffer (25 mM) at pH 7.5) for 15 min. The chip was rinsed with sodium phosphate buffer (25 mM) at pH 7.5 (2×20 mL), incubated in the same buffer for 15 min and subsequently overlaid with anti-RI chicken primary antibody and fluorescein-conjugated anti-chicken secondary antibody (1.5 µg/mL in sodium phosphate buffer (25 mM) at pH 7.5) for 30 min. The chip was rinsed with sodium phosphate buffer (25 mM) at pH 7.5 (2×20 mL) and incubated in the same buffer for 15 min. The chip was scanned with a Genomic Solutions® GeneTac UC4×4 Fluorescence Scanner using a gain of 50.

(ii) Ellipsometry: Ellipsometric measurements were performed to determine the optical thicknesses of the SAMs, RNase A, and RI on the surface. The measurements were performed using a wavelength of 632 nm and 70° angle of incidence. The optical thickness reported is the average of seven different locations on samples. A slab model was used to interpret these constants. The slab (SAM and protein) was assumed to have an index of refraction of 1.46 (ref).

Results and Discussion

Generation of phosphinothioester-displaying SAMs on gold. Carboxylic acid displaying gold surfaces were generated by incubating the gold surfaces in an ethanolic solution containing equimolar quantities of HS—(CH2)11-(O—CH2-CH2)6-O—CH2-COOH and HS—(CH2)11-(O—CH2-CH2)3-OH. The carboxylic acid functionalities were reacted with EDC/NHS and the resultant succinimidyl esters were converted into phosphinothioesters by reacting with phosphinomethanethiol. Phosphinomethanethiol was synthesized in multigram quantities according to an earlier published strategy [70]. Generation of phosphinothioester SAMs on the gold surfaces provides a highly ordered surface for performing Staudinger ligation. This surface is significantly more ordered than glass slides used earlier [5, 71] which enables the use of precise techniques like surface plasmon resonance [72] and liquid crystals [3, 73] for detection of ligand binding. The facile generation of phosphinothioesters directly on SAMs of alkanethiols on gold is a noteworthy contribution of this work.

Figure 7:
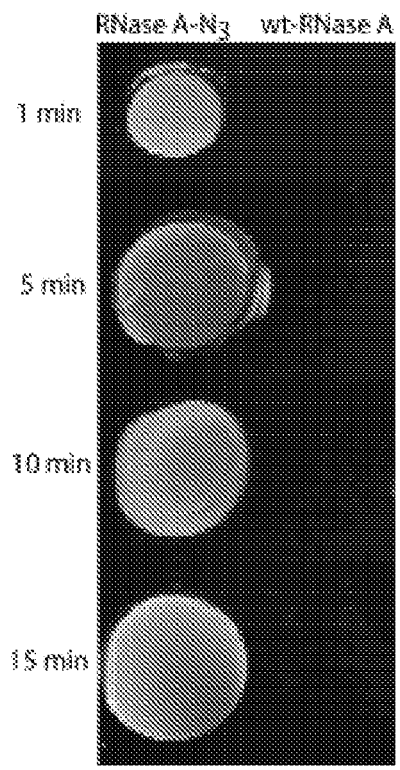
FIG. 7 is a figure illustrating the kinetics and specificity of immobilization of azido-RNase A as described in Example 7.

Azido-RNase A immobilization via Staudinger ligation. Azido-RNase A (in 5% DMF/water) was immobilized onto phosphinothioester chips via Staudinger ligation (FIG. 1). Incubation of wild-type RNase A on phosphinothioester chips did not result in any detectable RNase A immobilization (FIG. 7), thus establishing that azido-RNase A immobilization occurred exclusively via the azide functionality. Attempts at protein immobilization at various pH values without DMF were unsuccessful. DMF might be required for solubilization of the two hydrophobic phenyl groups on the phosphinothioester, and hence increasing accessibility to the azide functionality, thus enabling Staudinger ligation. We were concerned that derivatizing the alkane thiol monolayers with phosphinomethanethiol would result in a hydrophobic surface due to the introduction of two phenyl groups, thus increasing non-specific adsorption of proteins onto the surface. Indeed, long protein incubations (>1 hr) gave rise to noticeable non-specific protein attachment on the surface (data not shown). However, Staudinger ligation proceeded rapidly (fluorescence signal was detected as early as 1 minute into immobilization), and no significant non-specific interactions were observed in the time required for protein immobilization (FIG. 7).

Peptides, and to a much lesser extent, proteins, have been immobilized using bio-orthogonal approaches previously. For example, peptides have been covalently immobilized via imine [74], oxime [2], and semicarbazone [75] linkages. However, carbon-nitrogen double bonds of imines, oximes, and hydrazones are susceptible to hydrolysis [76, 77]. In contrast, our method of immobilization generates an amide linkage, one of the most stable linkages known in nature [78]. Diels-Alder cycloaddition [63, 79] has been used to immobilize peptides on surfaces. Another cycloaddition reaction, Huisgen's 1,3-dipolar cycloaddition, was used to immobilize proteins [63]. This reaction subjects proteins to harsh reaction conditions, namely, a Cu(I) catalyst, a potent reducing agent (TCEP) and a polytriazole ligand, which is not water soluble. These reaction conditions frequently cause protein precipitation [47, 66] which limits the general applicability of this reaction. A transient thioester intermediate involved in native chemical ligation and intein chemistry has been utilized in immobilizing peptides [80] and proteins [81] respectively. The immobilization results in the incorporation of a cysteine onto the immobilized species, which can be a center for undesirable side reactions. For example, cysteine is reactive towards electrophiles [14a, 14b, 82] and can undergo β-elimination [15] or disrupt SAMs on gold or silver surfaces [16]. A traceless approach to intein-mediated immobilization reported recently [83] utilizes split-intein chemistry, wherein the intein is spliced off resulting in the immobilization of the target protein. This method, although creative, is atomically uneconomical and entails exposing the surface to excessive protein mass (intein) which can produce background signals due to non-specific protein attachment.

Figure 8:
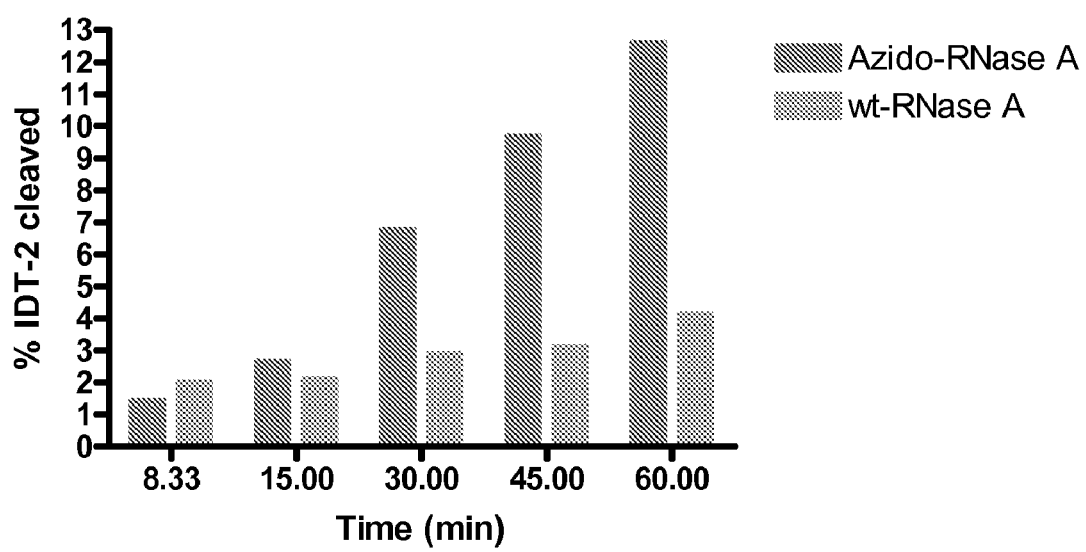
FIG. 8 is a graph showing the results of an activity assay on immobilized RNase A.

Activity assay on immobilized RNase A. Enzymatic activity assays were performed by incubating chips displaying immobilized RNase A in solutions containing a fluorogenic substrate of RNase A. The fluorescence intensity increased at a much faster rate for a phosphinothioester chip incubated with azido-RNase A than the one incubated with wild-type RNase A (FIG. 8). Thus, the enzyme was active after immobilization by Staudinger ligation. The small enzymatic activity detected on the phosphinothioester chip incubated with wild-type RNase A could be a consequence of non-specifically attached enzyme. Retention of enzymatic activity of the immobilized enzyme is noteworthy for potential applications that utilize immobilized enzymes as recyclable catalysts for industrial processes [84].

Figure 9A:
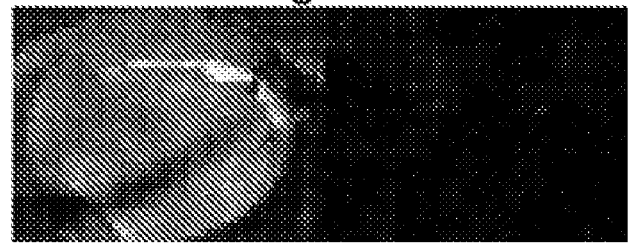
FIGS. 9A and 9B illustrate RI binding on immobilized RNase A as measured by (A) Immunoassay and (B) Ellipsometry as described in Example 7.
Figure 9B:
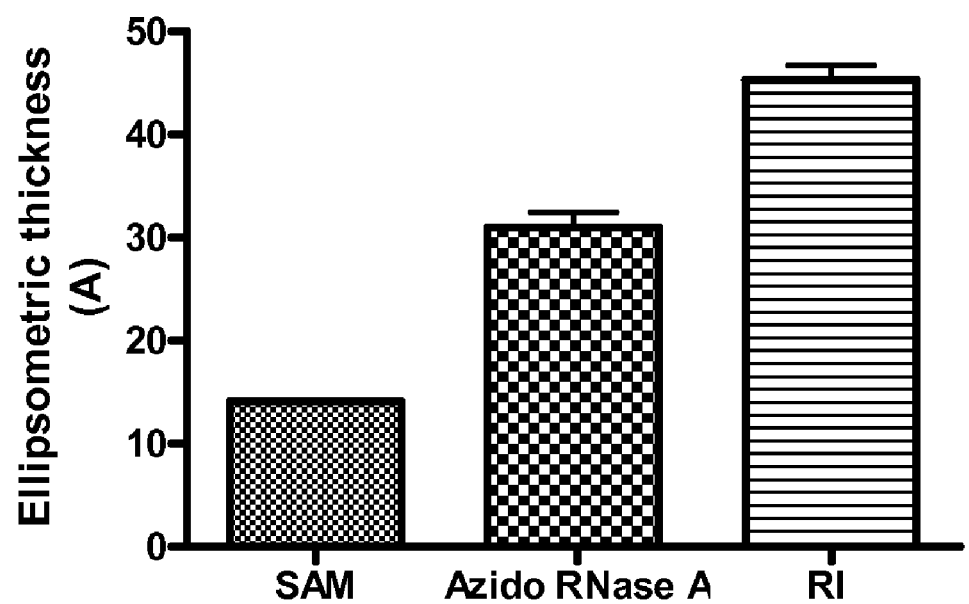

RI binding to immobilized RNase A. The binding of RI to immobilized RNase A was characterized by an immunoassay that involved a primary antibody to RI and a secondary fluorescent antibody (FIG. 9A). No RI binding was observed when the phosphinothioester chip incubated with wt-RNase A was overlaid with RI. This result demonstrates that the RI detected on the surface was bound to the immobilized RNase A and was not adhering to the surface via non-specific interactions. Ellipsometric measurements (FIG. 9B) corroborated these findings.

This example describes a general, facile and bio-orthogonal strategy for site-specific protein immobilization on SAMs on a gold surface. This method of protein immobilization can be used to generate oriented protein microarrays for high-throughput detection of binding partners for proteins and in diagnostic applications that detect disease markers in clinical samples.

REFERENCES

[1] G. MacBeath, S. L. Schreiber, Science 2000, 289, 1760-1763.
[2] J. R. Falsey, M. Renil, S. Park, S. Li, K. S. Lam, Bioconjug. Chem. 2001, 12, 346-353.
[3] Y.-Y. Luk, M. L. Tingey, K. A. Dickson, R. T. Raines, N. L. Abbott, J. Am. Chem. Soc. 2004, 126, 9024-9032.
[4] For reviews, see: a) C. J. A. Wallace, Protein Engineering by Semisynthesis, CRC Press, Boca Raton, Fla., 1999; b) R. L. Lundblad, Chemical Reagents for Protein Modification, 3rd ed., CRC Press, Boca Raton, Fla., 2005.
[5] M. B. Soellner, K. A. Dickson, B. L. Nilsson, R. T. Raines, J. Am. Chem. Soc. 2003, 125, 11790-11791.
[6] For a review, see: H. Paulus, Annu. Rev. Biochem. 2000, 69, 447-496.
[7] a) T. J. Tolbert, C.-H. Wong, J. Am. Chem. Soc. 2000, 122, 5421-5428; b) L. P. Tan, S. Q. Yao, Protein Pept. Lett. 2005, 12, 769-775.
[8] a) I. R. Cottingham, A. Millar, E. Emslie, A. Colman, A. E. Schnieke, C. McKee, Nat. Biotechnol. 2001, 19, 974-977; b) A. Borodovsky, H. Ovaa, N. Kolli, T. Gan-Erdene, K. D. Wilkinson, H. L. Ploegh, B. M. Kessler, Chem. Biol. 2002, 9, 1149-1159.
[9] a) L. H. Noda, S. A. Kuby, H. A. Lardy, J. Am. Chem. Soc. 1953, 75, 913-917; b) K. A. Connors, M. L. Bender, J. Org. Chem. 1961, 26, 2498-2504.
[10] For a review, see: P. E. Dawson, S. B. H. Kent, Annu. Rev. Biochem. 2000, 69, 923-960.
[11] For reviews, see: a) T. C. Evans, Jr., M.-Q. Xu, Chem. Rev. 2002, 102, 4869-4883; b) T. W. Muir, Annu. Rev. Biochem. 2003, 72, 249-289; c) V. Muralidharan, T. W. Muir, Nat. Methods 2006, 3, 429-438.
[12] R. Y. Lue, G. Y. Chen, Y. Hu, Q. Zhu, S. Q. Yao, J. Am. Chem. Soc. 2004, 126, 1055-1062.
[13] a) R. J. Wood, D. D. Pascoe, Z. K. Brown, E. M. Medlicoft, M. Kriek, C. Neylon, P. L. Roach, Bioconjug. Chem. 2004, 15, 366-372; b) A. Watzke, M. Kohn, M. Gutierrex-Rodriguez, R. Wacker, H. Schroder, R. Breinbauer, J. Kuhlmann, K. Alexandrov, C. M. Niemeyer, R. S. Goody, H. Waldmann, Angew. Chem. Int. Ed. Engl. 2006, 45, 1408-1412.
[14] a) C. H. Schneider, A. L. de Weck, Biochim. Biophys. Acta 1965, 168, 27-35; b) R. A. Bednar, Biochemistry 1990, 29, 3684-3690; c) R. T. Raines, Nat. Struct. Biol. 1997, 4, 424-427.
[15] M. Friedman, Adv. Exp. Med. Biol. 1999, 459, 145-159.
[16] W. Terrettax, W. P. Ulrich, H. Vogel, Q. Hong, L. G. Dover, J. H. Lakey, Protein Sci. 2002, 11, 1917-1925.
[17] For reviews, see: a) H. C. Hang, C. R. Bertozzi, Acc. Chem. Res. 2001, 34, 727-736; b) S. Bräse, C. Gil, K. Knepper, V. Zimmermann, Angew. Chem. Int. Ed. Engl. 2005, 44, 5188-5240.
[18] a) R. Huisgen, Angew. Chem. Int. Ed. Engl. 1963, 2, 565-598; b) H. C. Kolb, K. B. Sharpless, Drug Discov. Today 2003, 15, 1128-1137; c) D. J. V. C. van Steenis, O. R. P. David, G. P. F. van Strijdonck, J. H. van Maarseveen, J. N. H. Reek, Chem. Commun. 2005, 4333-4335.
[19] For reviews, see: a) M. Köhn, R. Breinbauer, Angew. Chem. Int. Ed. Engl. 2004, 43, 2-12; b) B. L. Nilsson, M. B. Soellner, R. T. Raines, Annu. Rev. Biophys. Biomolec. Struct. 2005, 34, 91-118.
[20] C. J. Noren, S. J. Anthony-Cahill, M. C. Griffith, P. G. Schultz, Science 1989, 244, 182-188.
[21] K. L. Kiick, E. Saxon, D. A. Tirrell, C. R. Bertozzi, Proc. Natl. Acad. Sci. U.S.A. 2002, 99, 19-24.
[22] H. K. Hall, J. Am. Chem. Soc. 1957, 79, 5441-5444.
[23] R. Kluger, J. C. Hunt, J. Am. Chem. Soc. 1984, 106, 5667-5670.
[24] D. Bonnet, N. Ollivier, H. Gras-Masse, O. Melnyk, J. Org. Chem. 2001, 66, 443-449.
[25] R. L. Hinman, J. Org. Chem. 1958, 23, 1587-1588.
[26] a) J. N. Brønsted, K. J. Pedersen, Z. physik. Chem. (Leipzig) 1924, 108, 185-235; b) D. J. Hupe, W. P. Jencks, J. Am. Chem. Soc. 1977, 99, 451-464.
[27] M. J. Gresser, W. P. Jencks, J. Am. Chem. Soc. 1977, 77, 6963-6970.

[28] E. A. Castro, C. Ureta, J. Org. Chem. 1989, 54, 2153-2159.
[29] W. P. Jencks, M. Gilchrist, J. Am. Chem. Soc. 1968, 90, 2622-2637.
[30] a) T. C. Bruice, J. J. Bruno, W.-S. Chou, J. Am. Chem. Soc. 1963, 85, 1659-1669; b) T. C. Bruice, A. Donzel, R. W. Huffman, A. R. Butler, J. Am. Chem. Soc. 1967, 89, 2106-2121; c) M. J. Gregory, T. C. Bruice, J. Am. Chem. Soc. 1967, 89, 2121-2127.
[31] E. Buncel, I.-H. Um, Tetrahedron 2004, 60, 7801-7825.
[32] J. Antosiewicz, J. A. McCammon, M. K. Gilson, J. Mol. Biol. 1994, 238, 415-436.
[33] W. P. Jencks, J. Carriuolo, J. Am. Chem. Soc. 1960, 82, 1778-1786.
[34] E. A. Castro, Chem. Rev. 1999, 99, 3505-3524.
[35] a) F. Lynen, E. Reichert, L. Rueff, Ann. Chem. 1951, 574, 1-32; b) T. C. Chou, F. Lipmann, J. Biol. Chem. 1952, 196, 89-103.
[36] a) T. C. Bruice, L. R. Fedor, J. Am. Chem. Soc. 1964, 86, 738-739; b) T. C. Bruice, L. R. Fedor, J. Am. Chem. Soc. 1964, 86, 739-740; c) T. C. Bruice, L. R. Fedor, J. Am. Chem. Soc. 1964, 86, 4886-4897.
[37] a) W. P. Jencks, J. Am. Chem. Soc. 1958, 80, 4581-4584; b) W. P. Jencks, J. Am. Chem. Soc. 1958, 80, 4585-4588.
[38] R. T. Raines, Chem. Rev. 1998, 98, 1045-1066.
[39] a) T. C. Evans, J. Benner, M. Q. Xu, Protein Sci. 1998, 7, 2256-2264; b) B. L. Nilsson, R. J. Hondal, M. B. Soellner, R. T. Raines, J. Am. Chem. Soc. 2003, 125, 5268-5269.
[40] R. J. Hondal, B. L. Nilsson, R. T. Raines, J. Am. Chem. Soc. 2001, 123, 5140-5141.
[41] a) U. Arnold, M. P. Hinderaker, B. L. Nilsson, B. R. Huck, S. H. Gellman, R. T. Raines, J. Am. Chem. Soc. 2002, 124, 8522-8523; b) U. Arnold, M. P. Hinderaker, J. Köditz, R. Golbik, R. Ulbrich-Hoffmann, R. T. Raines, J. Am. Chem. Soc. 2003, 125, 7500-7501.
[42] C. S. Yee, M. R. Seyedsayamdost, M. C. Chang, D. G. Nocera, J. Stubbe, Biochemistry 2003, 42, 14541-14552.
[43] J. R. Knowles, Science 1987, 236, 1252-1258.
[44] a) A. L. Murdock, K. L. Grist, C. H. W. Hirs, Arch. Biochem. Biophys. 1966, 114, 375-390; b) J. M. Messmore, D. N. Fuchs, R. T. Raines, J. Am. Chem. Soc. 1995, 117, 8057-8060.
[45] T. J. Rutkoski, E. L. Kurten, J. C. Mitchell, R. T. Raines, J. Mol. Biol. 2005, 354, 41-54.
[46] M. Cretich, F. Damin, G. Pirri, M. Chiari, Biomol. Eng. 2006, 23, 77-88.
[47] A. E. Speers, G. C. Adam, B. F. Cravaft, J. Am. Chem. Soc. 2003, 125, 4686-4687.
[48] Q. Wang, T. R. Chan, R. Hilgraf, V. V. Fokin, K. B. Sharpless, M. G. Finn, J. Am. Chem. Soc. 2003, 125, 3192-3193.
[49] J. W. Back, O. David, G. Kramer, G. Masson, P. T. Kasper, L. J. de Koning, L. de Jong, J. H. van Maarseveen, C. G. de Koster, Angew. Chem. Int. Ed. Engl. 2005, 44, 7946-7950.
[50] J. P. Danehy, K. N. Parameswaran, J. Chem. Eng. Data 1968, 13, 386-389.
[51] P. A. Leland, L. W. Schultz, B.-M. Kim, R. T. Raines, Proc. Natl. Acad. Sci. U.S.A. 1998, 98, 10407-10412.
[52] B. D. Smith, M. B. Soellner, R. T. Raines, J. Biol. Chem. 2003, 278, 20934-20938.
[53] Wilson, D. S.; Nock, S. Angew. Chem. Int. Ed. Engl. 2003, 42, 494-500.
[54] Merkel, J. S.; Michaud, G. A.; Salcius, M.; Schweitzer, B.; Predki, P. F. Curr. Opin. Biotechnol. 2005, 16, 447-52.
[55] Nature genetics 1999, 21, 1-60.
[56] Yeo, D. S.; Panicker, R. C.; Tan, L. P.; Yao, S. Q. Comb. Chem. High. Throughput Screen. 2004, 7, 213-21.
[57] Butler, J. E.; Ni, L.; Nessler, R.; Joshi, K. S.; Suter, M.; Rosenberg, B.; Chang, J.; Brown, W. R.; Cantarero, L. A. J. Immun. Methods 1992, 150, 77-90.
[58] Zhu, H.; Bilgin, M.; Bangham, R.; Hall, D.; Casamayor, A.; Bertone, P.; Lau, N.; Jansen, R.; Bidlingmaier, S.; Houfek, T.; Mitchell, T.; Miller, P.; Dean, R. A.; Gerstein, M.; Snyder, M. Science 2001, 293, 2101-2105.
[59] Paborsky, L. R.; Dunn, K. E.; Gibbs, C. S.; Dougherty, J. P. Anal. Biochem. 1996, 234, 60-5.
[60] Lahiri, J. I., L.; Tien, J.; Whitesides, G. M. Anal. Chem. 1999, 71, 777-790.
[61] Peluso, P.; Wilson, D. S.; Do, D.; Tran, H.; Venkatasubbaiah, M.; Quincy, D.; Heidecker, B.; Poindexter, K.; Tolani, H.; Phelan, M.; Witte, K.; Jung, L. S.; Wagner, P.; Nock, S. Anal. Biochem. 2003, 312, 113-124.
[62] Cha, T.; Guo, A.; Zhu, X. Y. Proteomics 2005, 5, 416-9.
[63] Sun, X. L.; Stabler, C. L.; Cazalis, C. S.; Chaikof, E. L. Bioconjug. Chem. 2006, 17, 52-7.
[64] Duckworth, B. P.; Xu, J.; Taton, T. A.; Guo, A.; Distefano, M. D. Bioconjug. Chem. 2006.
[65] Gauchet, C.; Labadie, G. R.; Poulter, C. D. J. Am. Chem. Soc. 2006.
[66] Kalia, J.; Raines, R. T. Chembiochem 2006, (submitted).
[67] Kohn, M.; Breinbauer, R. Angew. Chem. Int. Ed. Engl. 2004, 43, 2-12.
[68] Staudinger, H.; Meyer, J. Helv. Chim. Acta 1919, 2, 635-46.
[69] Nilsson, B. L.; Kiessling, L. L.; Raines, R. T. Org. Lett. 2001, 3, 9-12.
[70] Soellner, M. B.; Nilsson, B. L.; Raines, R. T. J. Org. Chem. 2002, 67, 4993-4996.
[71] Kohn, M.; Wacker, R.; Peters, C.; Schroder, H.; Soulere, L.; Breinbauer, R.; Niemeyer, C. M.; Waldmann, H. Angew. Chem. Int. Ed. Engl. 2003, 42, 5830-4.
[72] Green, R. J.; Frazier, R. A.; Shakesheff, K. M.; Davies, M. C.; Roberts, C. J.; Tendler, S. J. Biomaterials 2000, 21, 1823-35.
[73] Gupta, V. K.; Skaife, J. J.; Dubrovsky, T. B.; Abbott, N. L. Science 1998, 279, 2077-80.
[74] Huang, S.-C. P.; Caldwell, K. D.; Lin, J.-N.; Wang, H.-K.; Herron, J. N. Langmuir 1996, 12, 4292-4298.
[75] Duburcq, X.; Olivier, C.; Desmet, R.; Halasa, M.; Carion, O.; Grandidier, B.; Heim, T.; Stievenard, D.; Auriault, C.; Melnyk, O. Bioconjug Chem 2004, 15, 317-25.
[76] Johnson, R. W.; Stieglitz, J. J. Am. Chem. Soc. 1934, 56, 1904-1908.
[77] Cordes, E. H.; Jencks, W. P. J. Am. Chem. Soc. 1963, 85, 2843-2848.
[78] Radzicka, A.; Wolfenden, R. J. Am. Chem. Soc. 1996, 118, 6105-6109.
[79] Houseman, B. T.; Huh, J. H.; Kron, S. J.; Mrksich, M. Nat. Biotechnol. 2002, 20, 270-274.
[80] Lesaicherre, M. L.; Uttamchandani, M.; Chen, G. Y. J.; Yao, S. Q. Bioorg. & Med. Chem. Letters 2002, 12, 2079-2083.
[81] Lesaicherre, M. L.; Lue, R. Y.; Chen, G. Y.; Zhu, Q.; Yao, S. Q. J. Am. Chem. Soc. 2002, 124, 8768-9.
[82] Raines, R. T. Nature Structural Biology 1997, 4, 424-427.
[83] Kwon, Y.; Coleman, M. A.; Camarero, J. A. Angew. Chem. Int. Ed. Engl. 2006, 45, 1726-9.
[84] Chibata, I.; Tosa, T.; Sato, T.; Mori, T. Immobilized enzymes: Research and Development 1978, Chapter 4, 148-264.

[85] Backes, B. J.; Ellman, J. A. *J. Org. Chem.* 2000, 64, 2322-2330.

We claim:

1. A method for forming a covalent linkage between a peptide or protein and a chemical species comprising the steps of:
   (a) providing the peptide or protein functionalized with one or more thioester groups;
   (b) reacting one or more thioester groups of the peptide or protein functionalized with the one or more thioester groups with the hydrazine group of a hydrazine-functionalized chemical species of formula:

H$_2$N—NH—CH$_2$-M-L-R, wherein R is the chemical species, to form a hydrazide and thereby form a covalent linkage between the peptide or protein and the chemical species,
   wherein:
   R is a chemical species selected from an azido, alkenyl, alkynyl, nitrile or triazole group;
   M is a single bond or —C(O)NR'—, where R' is H, an alkyl, or an aryl, and L is an optional linker group which is an optionally substituted alkylene or an optionally substituted arylene linker.

2. The method of claim 1 wherein R is an azido group.

3. The method of claim 1 wherein M is a —C(O)NR'— group wherein R' is H, or an alkyl or an aryl group.

4. The method of claim 1 wherein L is present and L is an alkylene chain —(CH$_2$)$_n$— where n is an integer indicating the length of the chain, wherein one or more carbons of the chain are optionally substituted with a non-reactive or protected functional group which does not react with hydrazine and wherein one or more non-neighboring CH$_2$ groups are optionally replaced with S, CO, an ester, an amide group, an arylene group, or an N(R")$_2$ group, wherein R" is a hydrogen, an alkyl or an aryl group and at least one R" is not hydrogen.

5. The method of claim 1 wherein L is an alkylene chain —(CH$_2$)$_n$— where n is an integer ranging from 1 to 100.

6. The method of claim 1 wherein the covalent linkage is formed between the protein and the chemical species and the protein thioester is formed by intein-mediated splicing.

7. The method of claim 1 wherein the covalent linkage is formed at the C-terminus of the peptide or protein.

8. A method for immobilizing a peptide or protein to a surface which comprises the steps of:
   (a) forming a covalent linkage between a peptide or protein and a chemical species which is an azido group by the method of claim 2 wherein the hydrazine-functionalized chemical species is a compound of formula:

H$_2$N—NH—CH$_2$-M-L-R where R is an azido group to thereby form an azido-functionalized peptide or protein; and
   (b) reacting the azido-functionalized peptide or protein with a phosphinothioester which is covalently linked to the surface.

9. The method of claim 8 wherein a protein is immobilized to the surface and after immobilization the protein retains 80% or more of the activity of the protein prior to immobilization.

10. The method of claim 8 wherein two or more different peptides or proteins are immobilized to the surface.

11. The method of claim 8 wherein a plurality of different peptides or proteins are immobilized to the surface.

12. The method of claim 8 wherein the surface comprises a plurality of solid particles, resins or beads.

13. The method of claim 8 wherein the surface is a microarray.

14. The method of claim 1 wherein L is an alkylene chain —(CH$_2$)$_n$— where n is an integer ranging from 1 to 10.

15. The method of claim 14 wherein M is —C(O)NR'— and R' is H.

16. The method of claim 15 wherein R is an azido group.

17. The method of claim 1 wherein R is an azido group, M is —C(O)NR'— and R' is H.

18. The method of claim 1 wherein the reaction of the one or more thioester groups of the peptide or protein functionalized with the one or more thioester groups with the hydrazine group of the hydrazine-functionalized chemical species is carried out in aqueous buffer between pH 6-8.

19. The method of claim 1 wherein the hydrazine-functionalized chemical species is:

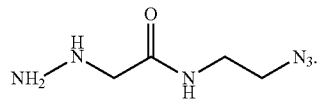

20. The method of claim 1 wherein R is an azido, nitrile or triazole group.

21. The method of claim 1 wherein R is an azido, alkenyl or alkynyl group.

22. The method of claim 1 wherein M is —C(O)NR'—, where R' is H or an alkyl group.

23. The method of claim 1 wherein L is an alkylene chain —(CH$_2$)$_n$— where n is an integer ranging from 2-4.

24. The method of claim 1 wherein L is —CH$_2$—CH$_2$—.

25. The method of claim 1 wherein R is an azido group, M is —C(O)NR'—, where R' is H, an alkyl or an aryl group and L is L is an alkylene chain —(CH$_2$)$_n$ where n is an integer ranging from 1 to 10.

26. The method of claim 1 wherein R is an azido group, M is —C(O)NR'—, where R' is H, an alkyl or an aryl group and L is —CH$_2$—CH$_2$—.

27. The method of claim 1 wherein R is an azido group, M is —C(O)NR'—, where R' is H, an alkyl or an aryl group and wherein L is present and L is an alkylene chain —(CH$_2$)$_n$— where n is an integer indicating the length of the chain, wherein one or more carbons of the chain are optionally substituted with a non-reactive or protected functional group which does not react with hydrazine and wherein one or more non-neighboring CH$_2$ groups are optionally replaced with S, CO, an ester or amide group, an arylene group, or an N(R")$_2$ group, wherein R" is a hydrogen, an alkyl or an aryl group and at least one R" is not hydrogen.

28. The method of claim 1 wherein M is —C(O)NR'—, R' is H, and L is —CH$_2$—CH$_2$—.

29. The method of claim 8 wherein L is an alkylene chain —(CH$_2$)$_n$— where n is an integer ranging from 1 to 10.

30. The method of claim 8 wherein L is an alkylene chain —(CH$_2$)$_n$— where n is an integer ranging from 2-4.

31. The method of claim 8 wherein L is —CH$_2$—CH$_2$—.

32. The method of claim 8 wherein M is —C(O)NR'—, where R' is H, an alkyl or an aryl group and wherein L is present and L is an alkylene chain —(CH$_2$)$_n$— where n is an integer indicating the length of the chain, wherein one or more carbons of the chain are optionally substituted with a non-reactive or protected functional group which does not react with hydrazine and wherein one or more non-neighboring CH$_2$ groups are replaced with S, CO, an ester or amide group, an arylene group, or an N(R")$_2$ group, wherein R" is a hydrogen, an alkyl or an aryl group and at least one R" is not hydrogen.

33. The method of claim 8 wherein M is —C(O)NR'—, where R' is H, or an alkyl group and L is present and is —(CH$_2$)$_n$—, where n is 1-100.

34. The method of claim 8 wherein M is —C(O)NR'—, where R' is H, or an alkyl group and L is present and is —(CH$_2$)$_n$—, where n is 1-10.

35. The method of claim 8 wherein M is —C(O)NR'—, where R' is H, or an alkyl group and L is present and is —(CH$_2$)$_n$—, where n is 2-4.

36. The method of claim 8 wherein the hydrazine-functionalized chemical species is:

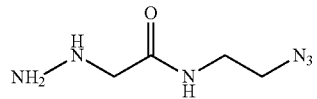

37. The method of claim 8 wherein the reaction of the azido-functionalized peptide or protein with the phosphinothioester covalently linked to the surface is carried out in aqueous buffer between pH 6-8.

* * * * *

UNITED STATES PATENT AND TRADEMARK OFFICE
CERTIFICATE OF CORRECTION

Page 1 of 1

PATENT NO. : 8,242,058 B2
APPLICATION NO. : 11/781838
DATED : August 14, 2012
INVENTOR(S) : Ronald T. Raines and Jeet Kalia It is certified that error appears in the above-identified patent and that said Letters Patent is hereby corrected as shown below:

In the Claims

In Claim 8, column 41, line 49, replace "method of claim 2" with --method of claim 1--.

In Claim 25, column 42, line 36, replace "L is L is an alkylene chain –(CH2)n" with --L is an alkylene chain –(CH2)n– --.

Signed and Sealed this
Seventeenth Day of June, 2014

Michelle K. Lee
*Deputy Director of the United States Patent and Trademark Office*